US007015341B2

(12) United States Patent
Franks

(10) Patent No.: US 7,015,341 B2
(45) Date of Patent: Mar. 21, 2006

(54) TRIACYLGLYCEROL OLIGOMER PRODUCTS AND METHODS OF MAKING SAME

(75) Inventor: William A. Franks, Kansas City, KS (US)

(73) Assignee: Franks Reserach Labs, Inc., Kansas City, KS (US)

( * ) Notice: Subject to any disclaimer, the term of this patent is extended or adjusted under 35 U.S.C. 154(b) by 0 days.

(21) Appl. No.: 10/943,437

(22) Filed: Sep. 17, 2004

(65) Prior Publication Data

US 2005/0054867 A1    Mar. 10, 2005

Related U.S. Application Data

(63) Continuation of application No. 10/718,910, filed on Nov. 21, 2003, now abandoned, which is a continuation of application No. 09/732,361, filed on Dec. 7, 2000, now Pat. No. 6,686,487.

(60) Provisional application No. 60/169,468, filed on Dec. 7, 1999.

(51) Int. Cl.
    *C07F 9/02*    (2006.01)
(52) U.S. Cl. ........................................ 554/83
(58) Field of Classification Search ............. 554/83
    See application file for complete search history.

(56) References Cited

U.S. PATENT DOCUMENTS

| 4,049,686 A | 9/1977 | Ringer et al. |
| 4,818,284 A | 4/1989 | McKelvey |
| 5,122,188 A | 6/1992 | Erhan et al. |
| 5,178,672 A | 1/1993 | Miller |
| 5,308,390 A | 5/1994 | Pennaz |
| 5,338,351 A | 8/1994 | Pennaz |

OTHER PUBLICATIONS

De Greyt, Kellens, and Huyghebaert, "Polymeric and oxidized triglyceride content of crude and refined vegetable oils", Fett/Lipid (1997), 99(8): 287-90.
Dijkstra and Van Opstal, "The Total Degumming Process," J.Am. Oil Chem. Soc., 66(7): 1002-1009 (Jul. 1989).
Diosady, L.L., "Scale-up of Canola Oil Degumming." Journal of American Oil Chemists Society, 61, Aug. 1984: No. 8.
Huang, Vegetable Oil-Based News Printing Ink Developed by continuous Polymerization Reaction, School of Chemical Engineering, Oklahoma State University, Stillwater, OK, May 1994.
Morrison and Boyd, Organic Chemistry, $5^{th}$ Ed., p. 1271.

*Primary Examiner*—Deborah D. Carr
(74) *Attorney, Agent, or Firm*—Dunlap, Codding & Rogers, P.C.

(57) ABSTRACT

The present invention relates generally to triacylglycerol oligomer products and methods of making, using and producing same.

5 Claims, 5 Drawing Sheets

TRIACYLGLYCEROL OLIGOMER PRODUCTS AND METHODS OF MAKING SAME

CROSS-REFERENCE TO RELATED APPLICATIONS

This application is a continuation of U.S. Ser. No. 10/718,910, filed Nov. 21, 2003 now abandoned, which is a continuation of U.S. Ser. No. 09/732,361, filed Dec. 7, 2000, now U.S. Pat. No. 6,686,487, which is a non-provisional of U.S. provisional patent application Ser. No. 60/169,468 filed Dec. 7, 1999, entitled "Vegetable Resin Products" and is hereby expressly incorporated herein by reference.

STATEMENT REGARDING FEDERALLY SPONSORED RESEARCH OR DEVELOPMENT

Not Applicable.

BACKGROUND OF THE INVENTION

1. Field of the Invention

The present invention relates generally to triacylglycerol oligomer products and methods of making, using and producing same.

2. Description of the Related Art

Triacylglycerols (TAGS) are lipids of plant or animal origin. They include such common substances as safflower oil, canola oil, peanut oil, corn oil, cottonseed oil, sunflower seed oil, linseed oil, soybean oil, tung oil, etc. Those TAGS that are liquids at room temperature are generally known as oils; those that are solids are usually known as fats. TAGS are simply the fatty acid esters of the triol glycerol. The general structure of TAGS is:

The fatty acids, $R_1$, $R_2$, $R_3$, that are obtained by hydrolysis of naturally occurring fats and oils are long, straight-chain carboxylic acids with about 12 to 20 carbon atoms. Most fatty acids contain even number of carbon atoms. Some of these common fatty acids are saturated, while others have one or more elements of unsaturation; generally carbon—carbon double bonds.

TAGS naturally occur in some plants and can be obtained in relative pure forms by various processing methods. Substances such as free fatty acids and phospholipids are removed during processing. TAGS resulting from a single plant source after processing is a mixture made up of TAGS with differing percentages of saturated and unsaturated fatty acids. Table 1 lists the approximate composition of the fatty acids obtained from hydrolysis of some TAGS. Table 2 lists the supply of major TAGS produced in the United States.

TABLE 1

| | Fatty Acid Composition Obtained by Hydrolyhsis of Common Triacylglycerols* | | | | | | |
|---|---|---|---|---|---|---|---|
| TAG | MYRISTIC | PALMITIC | STEARIC | OLEIC | LINOLEIC | ELEOSTEARIC | LINOLENIC |
| SOYBEAN | 1–2 | 6–10 | 2–4 | 20–30 | 50–58 | | 5–10 |
| COTTON SEED | 1–2 | 18–25 | 1–2 | 17–38 | 45–55 | | |
| CORN | 1–2 | 7–11 | 3–4 | 25–35 | 50–60 | | |
| LINSEED | | 4–7 | 2–4 | 14–30 | 14–25 | | 45–60 |
| SUNFLOWER | | 6–7 | 1–2 | 21–22 | 66–67 | | |
| TUNG | | | | | | 80 | |

TABLE 2

| Major TAGS produced in the United States | |
|---|---|
| TRIACYLGLYCEROL | PRODUCTION (POUNDS) |
| SOYBEAN | 20,220,000,000 |
| COTTONSEED | 1,210,000,000 |
| SUNFLOWERSEED | 1,196,772,000 |
| CORN | 1,283,200,000 |

TAGS containing multiple double bonds within their carboxylic acid moieties will undergo thermal polymerization to form oligomers which are low molecular weight polymers. Triacylglycerol Oligomers(TAGOS) were first described by Schieber (1928).

Several investigators, Schieber (1928, 1929), Kappelmier (1933, 1938), Kurz (1936), Bradley (1940), Phalnikar and Bhide (1944), Bradley (1947), Barker, Crawford, and Hilditch (1951), Wisenblatt, Wells, and Common (1953), Wells and Common (1953), Pascual and Detera (1966), Boelhouwer, Knegiel, and Tels (1967), Saha and Bandyopadhyay (1974), Sarma (1984) have suggested mechanisms for thermal polymerization of vegetable oils. Scheiber (1928, 1929) and Kappelmeier (1933, 1938) proposed a Diels-Alder diene synthesis as a basis for explaining the polymerization of vegetable oils which is often referred to in the literature. Most investigators agree with the formation of hydroxy unsaturated dimeric acids during thermal polymerization which are connected by means of a cyclic compound.

SUMMARY OF THE INVENTION

In one embodiment, the present invention is a method for degumming triacylglycerols. This method includes the steps of: Step A provides a degummer assembly including a tank member having an inlet and an outlet, and an interior reaction chamber. The inlet and the outlet are in open fluid communication with the interior reaction chamber. Step B introduces a triacylglycerol mixture into the interior reaction chamber of the degummer assembly via the inlet. Step C introduces a liquid medium at a predetermined temperature into the triacylglycerol mixture in the interior reaction chamber of the tank member, thereby causing at least two reaction products to form. Step D separates at least two reaction products resulting from the triacylglycerol mixture and the liquid medium. Step E removes at least two reaction products from the interior reaction chamber of the tank member via the outlet in the tank member.

DETAILED DESCRIPTION OF THE INVENTION

Figure 1:
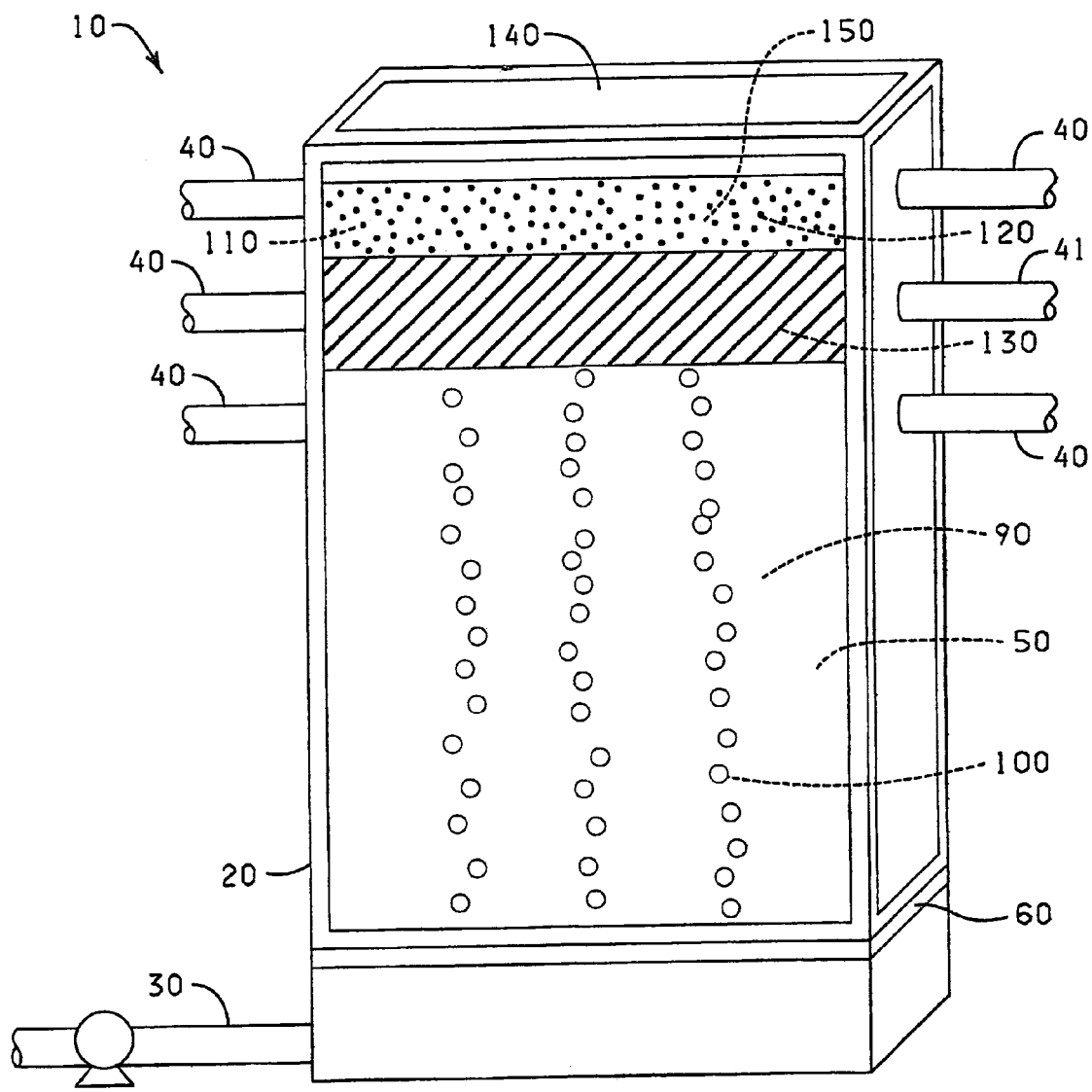
FIG. 1 is a perspective side view of the degummer assembly of the present invention.

Before explaining in detail at least one embodiment of the invention in detail by way of exemplary drawings, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for purpose of description and should not be regarded as limiting.

Removal of Lecithin (Degumming)

Lecithin is a mixture of phospholipids, cephalin and inositol phosphatides, glycerides, traces of tocopherols and pigments. Phospholipids are lipids that contain groups derived from phosphoric acid. The most common phospholipids are the phosphoglycerides, which are closely related to common fats and oils. A phosphoglyceride generally has a phosphoric acid group in place of one of the fatty acid groups of TAGS. The simplest class of lecithin are the phosphatidic acids, which consist of glycerol esterified by two fatty acids and one phosphoric acid group. Phosphatidic acid is represented by the chemical formula given below.

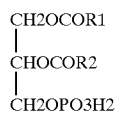

Lecithin can be hydrated with water which renders it immiscible with oil and can brings about a separation of hydrated lecithin and oil. However, hydrated lecithin when mixed thoroughly with water and TAGS forms a very stable emulsion that separates only on standing for long periods of time. Formation of the emulsion can be avoided by bubbling TAGS through a container filled with water. A bubble chamber (degummer) was developed for this purpose.

Figure 2:
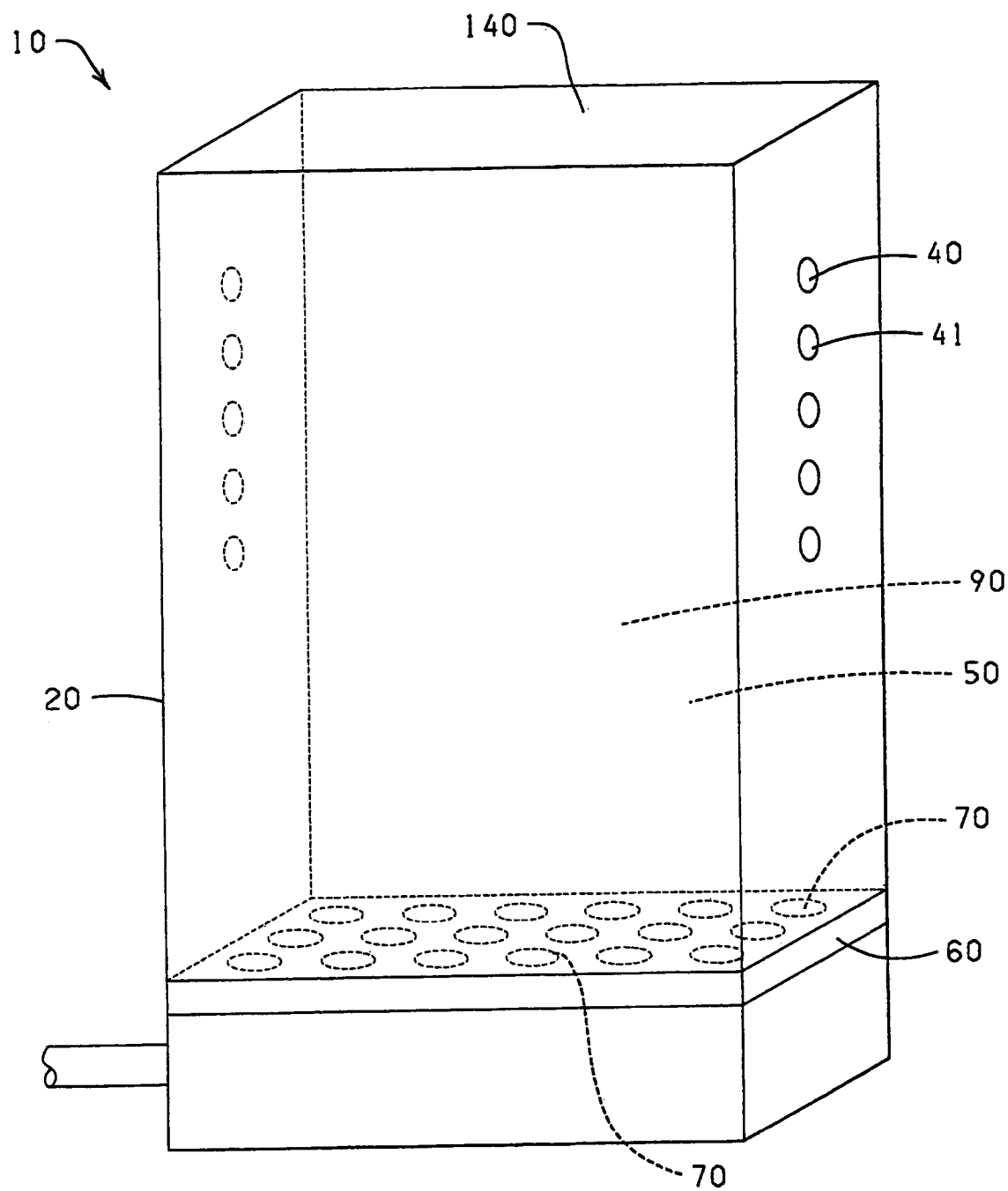
FIG. 2 is a second perspective side view of the degummer assembly of the present invention.

The degummer assembly 10 of the present invention is shown in FIGS. 1 and 2. The degummer assembly 10 consists of a tank member 20 having an inlet 30, at least one outlet 40, and an interior reaction chamber 50. The inlet 30 and the at least one outlet 40 are in open fluid communication with the interior reaction chamber 50. A plate 60 containing small holes 70 of known diameter is placed at the bottom 80 of the tank member 20 and attached to inlet 30. The interior reaction chamber 50 is filled with a liquid medium 90 such as water or other liquids (bulk liquid) and maintained at a temperature which can range from <25° C. to >60° C. Water hydrates the lecithin.

TAG is pumped or gravity fed into the interior reaction chamber 50 through the small holes 70 and form bubbles 100 or "strings" on contact with the liquid medium 90 and do not form emulsions. The small bubbles 100 or "strings" of TAGS rise to the surface of the bulk liquid and burst forming at least two separate liquid phases 110, (i.e., at least two reaction products) each of which remain separated from the liquid medium 90. At least one liquid phase contains degummed TAG 120, at least one liquid phase contains lecithin 130, and the third is the liquid medium 90.

As more and more TAG is fed into the tank member 20, the degummed TAG 120, which is less dense than the lecithin 130 rises to the top 140 of the interior reaction chamber 50 and forms a top layer 150. The lecithin 130 forms the middle layer. The lower layer is the liquid medium 90. The top layer 150 containing the degummed TAG 120 is allowed to reach a certain height to minimize contamination from the lecithin 130 at which time it can be continuously removed through the at least one outlet 40. The lecithin 130 can be removed through a lower at least one outlet tube 41. The volume produced depends on degummer assembly 10 variables such as the diameter of the small holes 70 of the inlet 30, size of the tank member 20, the flow rate, liquid medium 90 temperature, etc. Degummed TAG 120 was analyzed for phosphorous content. The results are given in Table 3 below.

TABLE 3

Phosphorous Content of Degummed Triacylglycerols (TAGS)

| TRIACYLGLYCEROL | PHOSPHOROUS, PPM* |
|---|---|
| SOYBEAN | 0.005 |

Van Nieuwenhuyzen (1976) has demonstrated that the viscosity of lecithin at a temperature of 70° C. increases as the moisture content decreases. The viscosity of the lecithin continues to increase until it achieves a moisture content of approximately 7%. The viscosity of the lecithin then begins to decrease rapidly until it is dry. This property of lecithin was used to develop a process to reduce the moisture content to less than 3%.

Figure 3:
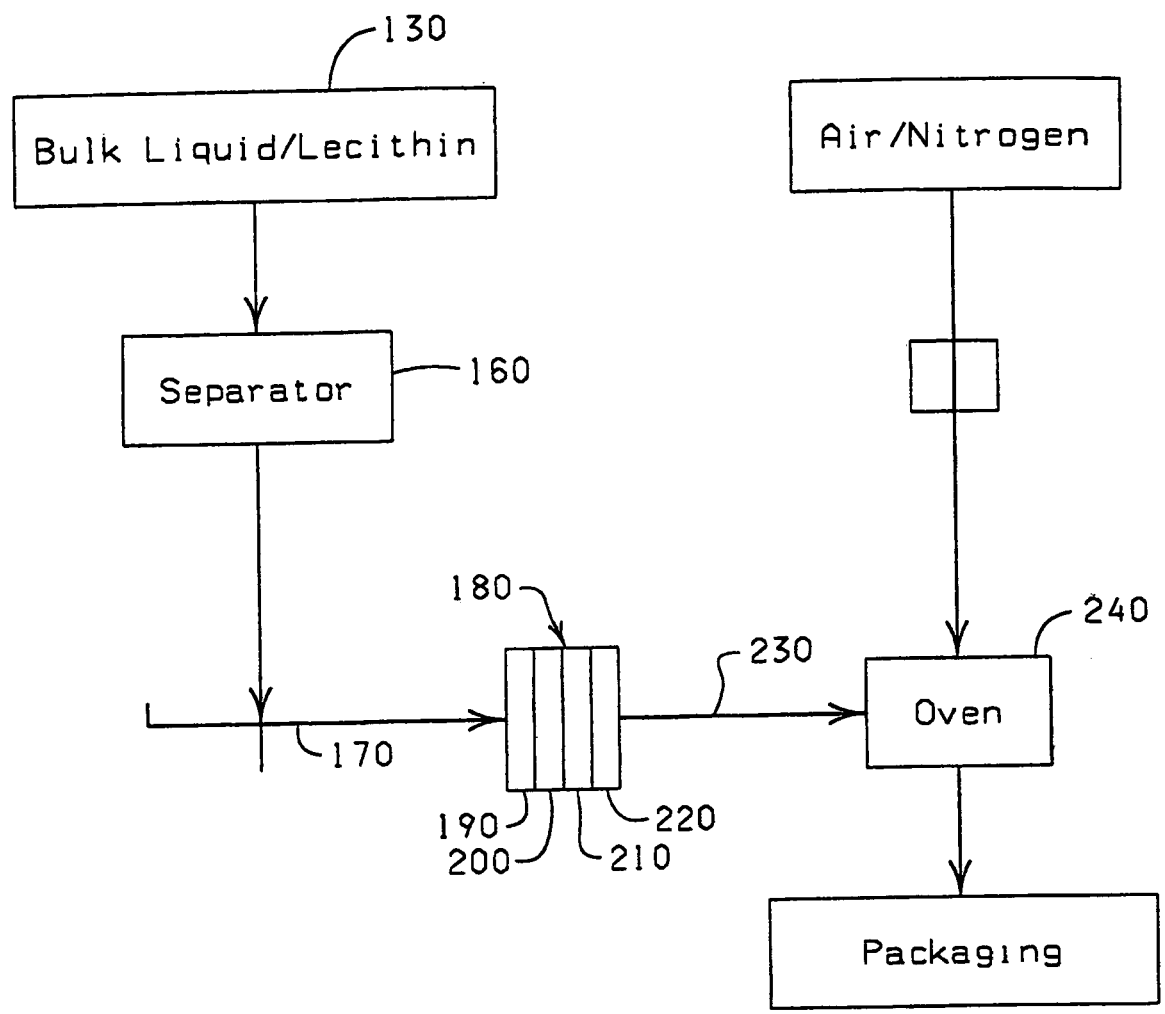
FIG. 3 is a schematic flow diagram.

Lecithin can be separated according to the flow diagram shown in FIG. 3. The lecithin 130 resulting from the degummer assembly 10 is passed into a separator or clarifier 160 to obtain a solids content of 15%. The concentrated lecithin mixture is then fed onto the porous cloth 170 of the conveyor system shown in FIG. 3. The porous cloth 170 allows the water to pass through while retaining the net lecithin 130. The net lecithin 130 is then passed through a series of pressurized and heated rollers 180 which are in contact with each other. The first 190 and second 200 roller systems are made of stainless steel. The third 210 and fourth 220 roller systems are made of hard rubber. As the lecithin 130 passes through the series of pressurized and heated rollers 180 moisture is removed bringing about changes in viscosity resulting in the formation of a lecithin sheet 230 that contains less than 5% moisture on exiting from the series of pressurized and heated rollers 180. The moist lecithin sheet 230 is passed through an oven 240 heated with air and the moisture content of the lecithin sheet 230 is further reduced to less than 3%.

TAGS that have been degummed according to the procedure given above are further refined by vacuum distillation of free fatty acids. The first step in the process is to remove under vacuum a large portion of the oxygen before heat is applied. Once the oxygen is removed under vacuum, heat is gradually applied until the boiling point temperature of free fatty acids have been reached at the operating vacuum. The temperature is maintained until all fatty acids have been removed. TAGS are now ready for thermal polymerization.

Figure 4:
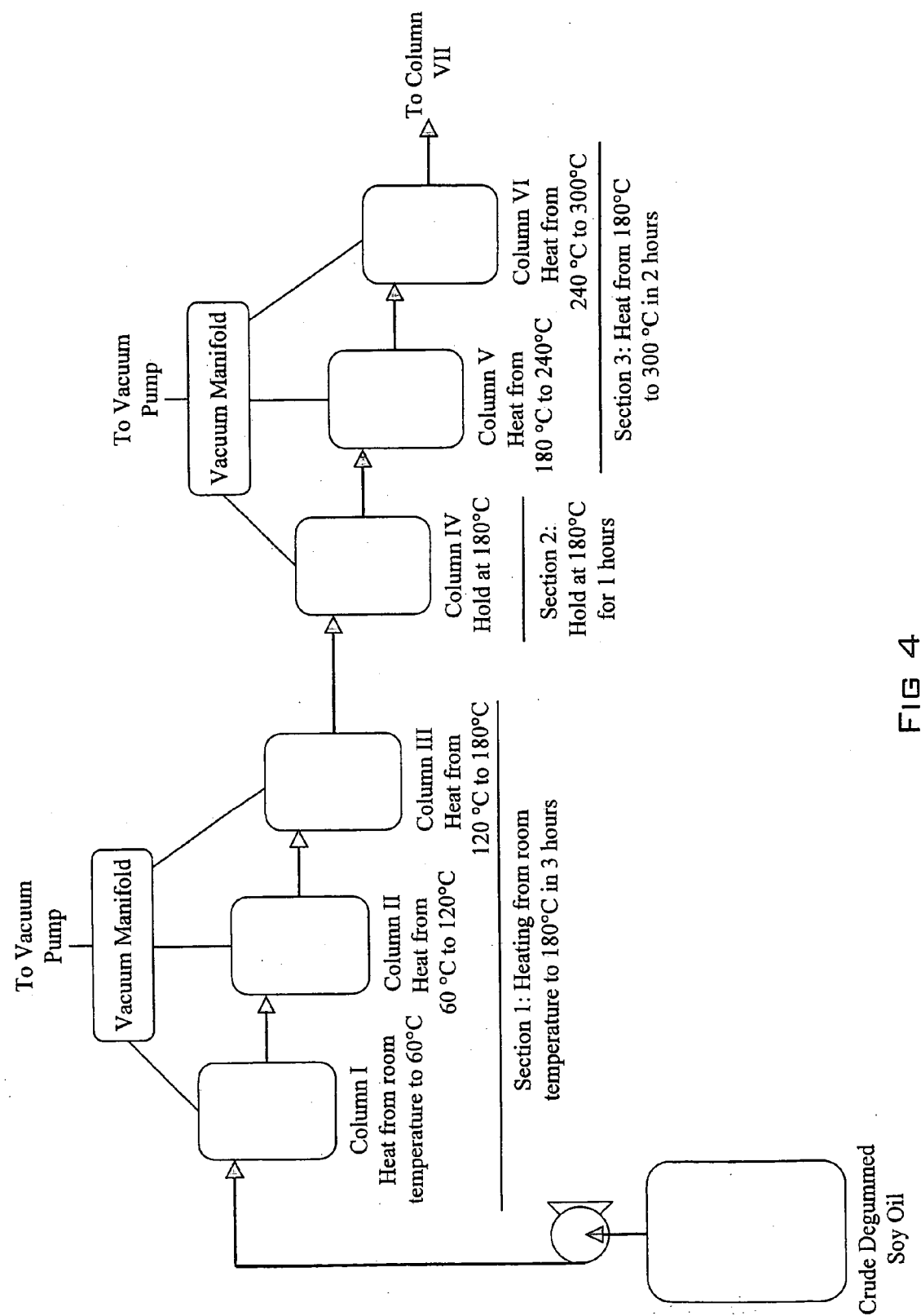
FIG. 4 is a flow diagram of the thermal polymerization process of TAGS.
Figure 4:
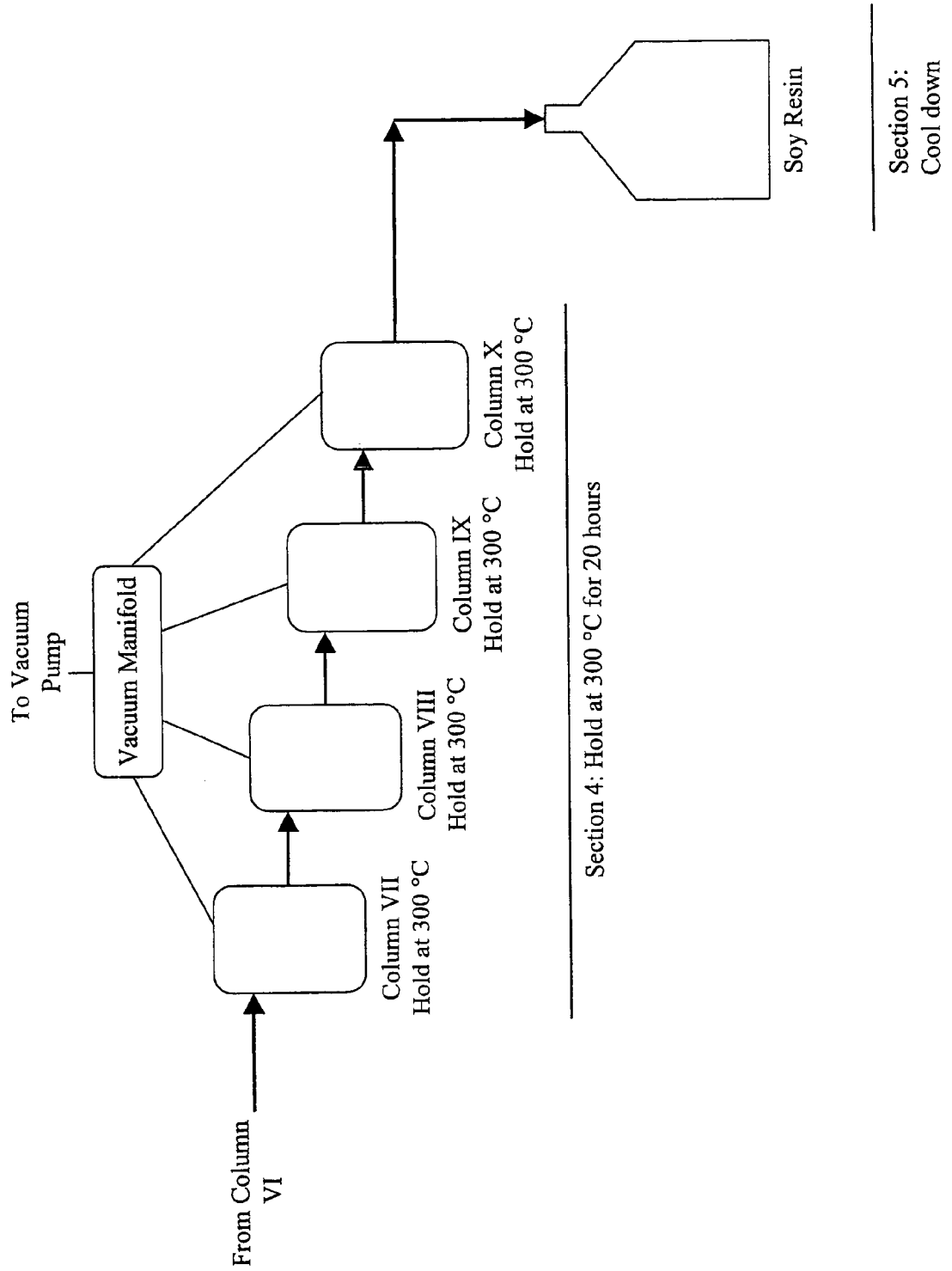

Referring to FIG. 4, a continuous semi-plugged flow reactor has been designed for the refining of TAGS. All columns are under the same vacuum. Degummed TAG at room temperature is pumped into a first column and removal of oxygen begins. As TAG flows upward through column once the temperature increases to 60° C., it exits into column two. As it flows upward through column two, oxygen is still being removed as the temperature gradually increases to 120° C. Columns three, four, and five are utilized for gradually increasing the TAG to the boiling point of free fatty acids at the operating vacuum and holding for a period of time depending on the flow rate to allow complete removal of the free fatty acids. At a temperature of 228° C.–235° C., TAG undergoes a color change from "straw" to a light greenish tint. The results are shown in Table 4.

TABLE 4

Data for Refined Triacylglycerols

| TRIACYLGLYCEROL | Y* | R* | B* | FREE FATTY ACID - %* |
|---|---|---|---|---|
| SOYBEAN | 2.8 | 1.4 | 92.0 | |
| COTTONSEED | | | | |
| SUNFLOWERSEED | | | | |
| CORN | | | | |

TAGOS are prepared by thermal polymerization of TAGS that have been degummed and refined according to the procedures given above. Pre-polymerization and polymerization takes place in columns six through ten shown.

Column six is the pre-polymerization reactor column wherein the temperature is gradually increased from the boiling point of the free fatty acids to polymerization temperature. TAG exits column six and enters column seven at the polymerization temperature. Columns seven, eight, nine and ten are the reactor columns and are maintained at the polymerization temperature. TAG remains in the reactor columns for a residence time depending on the flow rate and exits into the storage tanks that are also under the same vacuum. The viscosity attained will depend on the residence time (flow rate) and the polymerization temperature. The results are shown in Tables 5 and 6.

TABLE 5

Viscosities of Triacylglycerol Oligomers for Various Residence Times and Temperatures.

| TRIACYLGLYCEROL | RESIDENCE TIME | TEMP-ERATURE | VISCOSITY |
|---|---|---|---|
| SOYBEAN | 24 hours | 285 C. | 32 p |
| COTTONSEED | 8 hrs | 318 C. | 154 p |
| 50% | 13.5 hrs | 295 C. | 22 p |
| SUNFLOWERSEED + | | | |
| 50% SOYBEAN | | | |
| CORN | 13 hrs | 295 C. | 43 p |
| 50% SOYBEAN + | 13 hrs | 303 C. | 11 p |
| 50% CANOLA | | | |
| TUNG | | | |

TABLE 6

Viscosity and Molecular Weight of Triacylglycerols Oligomers

| TRIACYLGLYCEROL | VISCOSITY, CP | MOL. WEIGHT | MWD |
|---|---|---|---|
| SOYBEAN | 12400 | 132785 | 57.5 |
| SOYBEAN | 3207 | 5569 | 3.7 |

Skin color of face strongly depends on the type and amount of melanin and hemoglobin existing in the skin and varies widely according to several factors such as race, physiological conditions, age, sex, and seasonal variation. Face skin color is not uniform. It differs depending on whether it is the color of the forehead, forecheek, or sidecheek. Skin color was measured using photoelectric calorimeters and with the aid of computers, cosmetics were formulated using TAGOS to exactly match skin colors. The formulation given below were used to prepare cosmetic colors.

| Component | % |
|---|---|
| Standard No. 1 | |
| Cosmetic Brown-Lt | 5.00 |
| TAGOS Emulsion | 95.00 |
| Standard No. 2 | |
| Raw Sienna | 5.00 |
| TAGOS Emulsion | 95.00 |
| Standard No. 3 | |
| 85% cosmetic Green + | 5.00 |
| 15% Cosmetic Red | |
| TAGOS Emulsion | 95.00 |

An emulsion consisting of water and TAGOS was prepared using a lecithin sludge as the emulsifying agent. Lecithin sludge is the concentrated mixture of lecithin and water resulting from the degummer. TAGO, 62.7 gms, and lecithin sludge (50–60%), 21.2 gms, are mixed and heated to 70 C. Water, 176.8 gms, is heated in a separate container to 70° C. and then added to the TAGO and lecithin sludge mixture. The solution is stirred and allowed to cool. The pigment is added and the mixture is homogenized.

A Lovibond Tintometer was used to measure skin color. The instrument was standardized according to procedure using a gray scale and magnesium oxide standard. Measurements were made on the right cheek, left cheek, and the forehead. The skin color of 234 females was measured using the Lovibond Tintometer. This data is given in Table 9.

A thin layer of cosmetic preparation was placed on a filter paper and allowed to dry. The probe from the Lovibond Tintometer is placed directly on the dry cosmetic color preparation and the color determined and recorded. This data is given in Table 8.

A computer program was written for a Radio Shack Tridos 80 Computer to perform the calculations. Color matching functions of Banks (1977) were used to write the computer program. The program is written in four parts and is given in Table 7. The program produces tristimulus values, ratio of the standard cosmetic preparation to match the skin color, and the difference between the skin color and the calculated color match formulation. These results are given in Table 9.

TABLE 7

Computer Program for Color Matching - Four Parts

Part 1 ' FORMULA'

1 DIM TR(39), TY(39), TB(39), E(39), EY(39), EZ(39)
10 REM CALCULTAION OF CHROMATICITY COORDINATRES AND TRISTIMULUS
VALUES CALL TRISTIM
20 REM READ LOVIBOND SPECTRAL INTERNAL TRANSMITTANCES
40 FOR I = 0 TO 39
50 READ TR(I), TY(I), TB(I)
60 NEXT
70 REM READ CIE 1931 COLOR-MATCHING FUNCTIONS WEIGHTED BY
RELATIVE SPECTRAL POWER DISTRIBUTIONS OF CIE STANDARDS
80 FOR I = 0 TO 39
90 READ EX(I), EY(I), EZ(I)
100 NEXT
130 DATA .90258, .02889, .99815
131 DATA .90352, .12593, .99809
132 DATA .90439, .25435, .99788
133 DATA .90603, .39957, .99711
134 DATA .90737, .52037, .99573
135 DATA .90824, .61634, .99363
136 DATA .90886, .70289, .99111
137 DATA .90858, .77822, .98800
138 DATA .90722, .84481, .98338
139 DATA .90444, .89471, .97459
140 DATA .89819, .92976, .96004
141 DATA .88633, .95277, .94109
142 DATA .86526, .96755, .92316
143 DATA .83257, .97738, .89900
144 DATA .79598, .98364, .87326
145 DATA .77392, .98754, .84574
146 DATA .78952, .99040, .83553
147 DATA .83317, .99195, .85049
148 DATA .87817, .99236, .86792
149 DATA .91300, .99247, .85702
150 DATA .93628, .99179, .81808
151 DATA .95268, .99073, .77002
152 DATA .96362, .98933, .76498
153 DATA .97109, .98768, .77420
154 DATA .97648, .98599, .77827
155 DATA .98053, .98438, .77386
156 DATA .98348, .98333, .76119
157 DATA .98572, .98287, .76656
158 DATA .98753, .98279, .78191
159 DATA .98892, .98330, .83172
160 DATA .99012, .98405, .88572
161 DATA .99117, .98449, .93507
162 DATA .99194, .98510, .96744
163 DATA .99247, .98627, .98466
164 DATA .99303, .98789, .99228
165 DATA .99336, .98912, .99587
166 DATA .99365, .99014, .99719
167 DATA .99402, .99108, .99770
168 DATA .99420, .99160, .99790
169 DATA .99430, .99210, .99800
180 DATA .004, .000, .020
181 DATA .019, .000, .089
182 DATA .085, .002, .404
183 DATA .329, .009, 1.57

TABLE 7-continued

Computer Program for Color Matching - Four Parts

184 DATA 1.238, .037, 5.949
185 DATA 2.997, .122, 14.628
186 DATA 3.975, .262, 19.938
187 DATA 3.915, .443, 20.638
188 DATA 3.362, .694, 19.299
189 DATA 2.272, 1.058, 14.972
190 DATA 1.112, 1.618, 9.461
191 DATA .363, 2.358, 5.274
192 DATA .052, .3.401, 2.864
193 DATA .089, 4.833, 1.520
194 DATA .576, 6.462, .712
195 DATA 1.523, 7.934, .388
197 DATA 4.282, 9.832, .086
198 DATA 5.880, 9.841, .039
199 DATA 7.322, 9.147, .020
200 DATA 8.417, 7.992, .016
201 DATA 8.984, 6.627, .010
202 DATA 8.949, 5.316, .007
203 DATA 8.325, 4.176, .002
204 DATA 7.070, 3.153, .002
205 DATA 5.309, 2.190, .000
206 DATA 3.693, 1.443, .000
207 DATA 2.349, .886, .000
208 DATA 1.361, .504, .000
209 DATA .708, .259, .000
210 DATA .369, .134, .000
211 DATA .171, .062, .000
212 DATA .082, .029, .000
213 DATA .039, .014, .000
214 DATA .019, .006, .000
215 DATA .008, .003, .000
216 DATA .004, .002, .000
217 DATA .002, .001, .000
218 DATA .001, .001, .000
219 DATA .001, .000, .000
300 REM CALCULATIONS OF TRISTIMULUS VALUES
310 U = 0
320 V = 0
330 W = 0
340 PRINT "INPUT Y" : INPUT Y
350 PRINT "INPUT R" : INPUT R
360 PRINT "INPUT B" : INPUT B
370 FOR I = 0 TO 39
380 RYB = ((TR(I))[R]*((TY(I)[Y))*((TB(I)[B))
390 U = U + ( RYB * EX(I))
400 V = V + ( RYB + EY(I))
410 W = W + ( RYB + EZ(I))
420 NEXT
430 UVW = U + V + W
440 UBAR = U/UVW
450 VBAR = V/UVW
460 WBAR = W/UVW
470 X = U: LPRINT "X = ";X
480 Y1 = V: LPRINT "Y = ";Y1
490 Z = W: LPRINT "Z = ";Z
500 OPEN "O",1, "VALUES"
510 PRINT#1,X;Y1;Z
520 CLOSE 1
530 OPEN"O",1,"LOVIBOND"
540 PRINT#1,Y;R;B
550 CLOSE 1
560 RUN "FORMULA1"
Part 2 'FORMULA1'

10 DIM TR(15), TY(15), TB(15), ME(16,3), T(16,3), Y(3), R(3), B(3), F(1),
D(16,16)
40 FOR I = 0 TO 15
50 READ TR(I), TY(I), TB(I)
60 NEXT
132 DATA .90439, .25435, .99788
134 DATA .90737, .52037, .99573
136 DATA .90886, .70289, .99111
138 DATA .90722, .84481, .98338
140 DATA .89819, .92976, .96004
142 DATA .86526, .96755, .92316
144 DATA .79598, .98364, .87326

TABLE 7-continued

Computer Program for Color Matching - Four Parts

146 DATA .78952, .99040, .83553
148 DATA .87817, .99236, .86792
150 DATA .93628, .99179, .81808
152 DATA .96362, .98933, .76498
154 DATA .97648, .98599, .77827
156 DATA .98348, .98333, .76119
158 DATA .98753, .98279, .78191
160 DATA .99012, .98405, .88572
162 DATA .99194, .98510, .96744
330 FOR I = 1 TO 3
350 READ Y(I), R(I), B(I)
355 LPRINT " ":LPRINT Y(I), R(I), B(I)
360 NEXT
365 LPRINT " ":LPRINT "T1", "T2", "T3"
367 OPEN"O",1,"DYES"
370 J = 0
380 FOR I = 0 TO 15
385 J = J + 1
390 FOR N = 1 TO 3
410 Q = (TR(I)[R(N))*(TY(I)[Y(N))*(TB(I)[(N))
420 T(J,N) = (1−Q)[2/(2*Q)
430 NEXT
440 PRINT#1, T(J,1); T(J,2); T(J,3)
445 LPRINT " " : LPRINT T(J,1), T(J,2) T(J,3)
450 NEXT
460 CLOSE 1
465 GOTO 600
470 J = 0
480 OPEN "O",1,"SAMPLE"
505 LPRINT " ": LPRINT "F", "D"
510 FOR I = 0 TO 15
520 J = J + 1
530 Q = (TR(I)[X2)*(TY(I)[X1)*(TB(I)[X3)
540 F(J) = (1−Q)[2/(2*Q)
550 D(J,J) = −((4*Q)*(1−Q)+((1−Q)[2)*2)/(4*(Q[2))
560 PRINT#1, F(J);D(J,J)
565 LPRINT " ":LPRINT F(J), D(J,J)
570 NEXT
580 CLOSE 1
590 RUN "FORMULA2"
600 OPEN"I",1,"LOVIBOND"
610 INPUT#1,X1,X2,X3
620 CLOSE 1
630 GOTO 470
700 DATA 1.9, 3.7, 0
710 DATA 3.6, 4.0, 0
720 DATA 1.4, 1.2, 0
Part 3 "FORMULA2"

100 DIM ME(16,3), D(16,16), B(3,16), M(3,16),
F(16,1), R(3,3), A(3,3),
V(3,1),T(16,3), C(3,1)
105 LPRINT " ": LPRINT "EX-BAR, "EY-BAR", "EZ-BAR"
110 OPEN"I",1, "FUNCTION"
120 FOR I = 1 TO 16
140 INPUT#1, M(1,I), M(2,I), M(3,I)
170 NEXT
180 CLOSE 1
190 OPEN "1",1,"SAMPLE"
200 FOR I = 1 TO 16
210 INPUT#1, F(I,1), D(I,1)
215 D(I,1), = 1/D(I,1)
220 NEXT
230 CLOSE 1
240 FOR 1 = 1 TO 3
250 FOR J = 1 TO 16
260 B(I,J) = 0
270 FOR K = 1 TO 16
280 B(I,J) = B(I,J) + M(I,K)*D(K,J)
290 NEXT K
300 NEXT J
310 NEXT I
315 FOR J = 1 TO 16
316 LPRINT " ":LPRINT B(1,J),B(2,J),B(3,J)
317 NEXT
320 OPEN "I",1,"DYES"
330 FOR I = 1 TO 16

TABLE 7-continued

Computer Program for Color Matching - Four Parts

340 INPUT#1, T(I,1), T(I,2), T(I,3)
350 NEXT
360 CLOSE 1
370 FOR I = 1 TO 3
380 FOR J = 1 TO 3
390 R(I,J) = 0
400 FOR K = 1 TO 16
410 R(I,J) = R(I,J) + B(I,K)*T(K,J)
420 NEXT K
430 NEXT J
440 NEXT I
445 GOSUB 1000
450 GOSUB 18000
460 FOR I = 1 TO 3
470 C(I,1) = 0
480 FOR K = 1 TO 16
490 C(I,1) = C(I,1) + B(I,K)*F(K,1)
500 NEXT K
510 NEXT I
520 FOR I = 1 TO 3
530 V(I,1) = 0
540 FOR K = 1 TO 3
550 V(I,1) = V(I,1) + A(I,K)*C(K,1)
560 NEXT K
570 NEXT I
580 LPRINT " C1 EQUALS " ; V(1,1): LPRINT " "
590 LPRINT " C2 EQUALS " ; V(2,1): LPRINT " "
600 LPRINT " C3 EQUALS " ; V(3,1): LPRINT " "
610 OPEN "O",1, "INVERSE"
620 FOR I = 1 TO 3
630 PRINT#1, A(I,1);A(I,2);A(I,3)
640 NEXT
650 CLOSE 1
660 OPEN "O",1, "CONCN"
670 PRINT#1, V(1,1); V(2,1); V(3,1)
680 CLOSE 1
690 RUN "FORMULA3"
1000 PRINT "THE MATRIX TO BE INVERTED IS: ": PRINT
1010 FOR I = 1 TO 3: FOR J = 1 TO 3 : LPRINT R(I,J):
NEXT J: PRINT :
NEXT I
1020 RETURN
18000 CLS: REM SUBROUTINE TO INVERT AN N × N
MATRIX. A(N,N) IS THE
INPUT
18001 GOTO 18009: INPUT "DO YOU WANT DOUBLE
PRECISION";A$
18002 IF LEFT$(A$,1) = "N" THEN 18009
18004 DEFDBL A-H, O-Z
18009 DEFINT I,J,N
18010 N = 3
18050 FOR I = 1 TO N: A(I,1) = 1: NEXT
18052 CLS: PRINT " YOUR MATRIX IS: ": PRINT
18054 FOR I = 1 TO N: FOR J = 1 TO N: I3!=R(I,J):PRINT I3!;
:NEXT:PRINT :NEXT
18060 I1 = I1 + 1: IF I1 = N + 1 THEN 18210:
REM WE'RE THROUGH!
18070 IF R(I1,I1) = 0 THEN GOSUB 18130 :
REM INTERCHANGE ROWS
18080 REM NORMALIZE DIAGONAL ELEMENT AND ZERO
COLUMN IN OTHER
ROWS.
18090 Q = R(I1,I1): FOR J = I1 TO N: R(I1,J) = R(I1,J)/Q: NEXT
18095 FOR J = 1 TO N: A(I1,J) = A(I1,J)/Q: NEXT
18100 FOR I = 1 TO N: IF I = I1 THEN 18117
18105 Q = R(I,I1)
18110 FOR J = I1 TO N: R(I,J) = R(I,J) − Q*R(I1,J): NEXT
18115 FOR J = 1 TO N: A(I,J)=A(I,J)−Q*A(I1,J): NEXT
18117 NEXT I
18120 GOTO 18060
18130 REM INTERCHANGE ROWS TO PREVENT ZERO
DIVIDE
18140 I2 = I1: IF I2 = N THEN 18170
18150 I2 = I2 + 1: IF I2 = N THEN 18170
18160 IF R(I2,I1) = 0 AND I2<N THEN 18150
18170 IF I2= N THEN PRINT " DETERMINENT = 0 ! ! ! ": STOP
18180 FOR I = I1 TO N

TABLE 7-continued

Computer Program for Color Matching - Four Parts

```
18190 T = R(I1,I):R(I1,I) = R(I2,I): R(I2,I) = T
18200 S = A(I1,I):A(I1,I) = A(I2,I):A(I2,I) = S:NEXT: RETURN
18210 GOSUB 18230; FOR I = 1 TO N: FOR J = 1 TO N:
PRINT A(I,J): NEXT
J: PRINT:
18220 RETURN
18230 PRINT " THE INVERSE OF YOUR MATRIX IS : ":
PRINT:RETURN
19000 REM INPUT ELEMENTS BY ROW
19010 PRINT "ENTER THE ELEMENTS ONE AT A TIME
BY ROW AND PRESS
ENTER"
19020 FOR I = 1 TO N: FOR J = 1 TO N
19030 INPUT R(I,J): NEXT J,I
19040 GOTO 18050
Part 4 'FORMULA3'

100 DIM FM(16,1), TM(3,1), T(16,3), V(3,1) M(3,16), RM(16,1)
110 OPEN "I",1, "DYES"
120 FO;R i = 1 TO 16
130 INPUT#1, T(I,1), T(I,2), T(I,3)
140 NEXT
150 CLOSE 1
160 OPEN "I",1, "CONCN"
170 INPUT#1, V(1,1), V(2,1), V(3,1)
180 CLOSE 1
190 FOR I = 1 TO 16
200 FM(I,1) = 0
210 J = 1 TO 3
220 FM(I,1) = FM(I,1) + T(I,J) + V(J,I)
230 NEXT J
240 NEXT I
250 GOTO 500
260 OPEN "I",1, "FUNCTION"
270 FOR I = 1 TO 16
280 INPUT#1, M(1,I), M(2,I), M(3,I)
290 NEXT
300 CLOSE 1
310 FOR I = 1 TO 3
320 TM(I,1) = 0
330 FOR K = 1 TO 16
340 TM(I,1) = TM(I,1) + M(I,K)*RM(K,I)
350 NEXT K
360 NEXT I
370 OPEN " O",1, "TRISTIM"
380 PRINT#1, TM(1,1);TM(2,1);TM(3,1)
390 CLOSE 1
400 LPRINT " " : LPRINT " "
410 LPRINT "TRISTIMULUS VALUES FOR MATCH":
LPRINT " "
420 LPRINT " X = "; TM(1,1):LPRINT " "
430 LPRINT " Y = "; TM(2,1):LPRINT " "
440 LPRINT " Y="; TM(3,1):LPRINT " "
450 RUN "FORMULA4"
500 FOR I = 1 TO 16
510 B1 = 2*(1+FM(I,1))
520 B2 = B1[2
530 RM(I,1) = (B1 − SQR(B2−4))/2
540 NEXT
550 GOTO 260
Part 5 "FORMULA4"

6000 REM CALCULATIONS OF COLOR DIFFERENCE
6005 DIM DT(3,1), TM(3,1), A(3,3), DC(3,1),
V(3,1), VXS(1), VYS(1),
VZS(1)
6010 PRINT "INPUT VX, VY, VZ FOR SAMPLE"
6020 INPUT VXS(1), VYS(1), VZS(1)
6060 PRINT "INPUT VX, VY, VZ FOR MATCH"
6065 INPUT MXV: INPUT MYV: INPUT MZV
6067 FOR I = 1 TO 1
6210 DVY = ((0.23)*(VYS(I) − MYV))[2
6215 D1VXY = (( VXS(I) − VYS(I)) − (MXV −MYV))[2
6220 D2VZYY = (VZS(I) −VYS(I)) − (MZV − MYV)
6225 D3VZY = ((0.4)*(D2VZYY))[2
6230 DE = (DVY + D1VXY + D3VZY)[(1/2)
6235 DE = 40*DE
6237 NEXT
6238 LPRINT " "; LPRINT " "
62440 LPRINT " THE VALUE FOR THE COLOR
DIFFERENCE IS "; DE; LPRINT
" "
6250 PRINT " TO CONTINUE ITERATION , 'ENTER' 1. ": PRINT " "
6260 PRINT " TO DISCONTINUE ITERATION, 'ENTER' 2. ":
PRINT " "
6270 INPUT ZZ
6280 ON ZZ GOTO 10000, 6300
6300 END
10000 OPEN "I", 1,1 "VALUES"
10010 INPUT#1, X, Y, Z
10020 CLOSE 1
10030 OPEN "I",1, "TRISTIM"
10040 INPUT#1, TM(1,1), TM(2,1), TM(3,1)
10050 CLOSE 1
10060 DT(1,1) = X − TM(1,1)
10070 DT(2,1) = Y − TM(2,1)
10080 DT(3,1) = Z − TM(3,1)
10090 OPEN "I" ,1, "INVERSE
10100 FOR I = 1 TO 3
10110 INPUT#1, A(I1,). A(I2,), A(I3)
10120 NEXT
10130 CLOSE 1
10140 FOR I = 1 TO 3
10150 DC(I,1) = 0
10160 FOR K = 1 TO 3
10170 DC(I,1) = DC(I,1) + A(I,K)*DT(K,I)
10180 NEXT K
10190 NEXT I
10200 OPEN "I",1, "CONCN"
10210 INPUT#1, V(1,1), V(2,1), V(3,1)
10220 CLOSE 1
10230 V(1,1) = V(1,1) + DC(1,1)
10240 V(2,1) = V(2,1) + DC(2,1)
10250 V(3,1) = V(3,1) + DC(3,1)
10260 LPRINT " "; LPRINT " "
10270 LPRINT " C1 = ";V(1,1) : LPRINT " "
10280 LPRINT " C2 = ";V(2,1) : LPRINT " "
10290 LPRINT " C3 = ";V(3,1) : LPRINT " "
10300 OPEN "O",1, "CONCN"
10310 PRINT#1, V(1,1), V(2,1), V(3,1)
10320 CLOSE 1
10330 RUN "FORMULA3"
10340 END
```

TABLE 8

Color of Standard Soybean Cosmetic Formulations -

| NUMBER | Y | R | B |
| --- | --- | --- | --- |
| 1 | 1.9 | 3.7 | 0 |
| 2 | 3.6 | 4 | 0 |
| 3 | 1.3 | 1.2 | 0 |

TABLE 9

Skin Color of Females-

| NUM | COLOR | RANGE | HUE | VALUE | CHR | X-BAR | Y-BAR | Z-BAR | Y | DE |
|---|---|---|---|---|---|---|---|---|---|---|
| 12 | 1 | 1 | 7.53 YR | 4.86 | 4.03 | 0.4034 | 0.3733 | 0.2234 | 19 | 1–4 |
| 29 | 2 | 2 | 6.79 YR | 4.43 | 3.54 | 0.4 | 0.3619 | 0.2388 | 15 | 4–7 |
| 13 | 3 | 2 | 6.63 YR | 6 | 3.5 | 0.3761 | 0.3563 | 0.2677 | 30 | 11–12 |
| 12 | 4 | 4 | 5.29 YR | 3.59 | 2.99 | 0.3964 | 0.356 | 0.2546 | 10 | 7–9 |
| 15 | 5 | 4 | 5 YR | 5.34 | 3.75 | 0.3848 | 0.3562 | 0.259 | 23 | 9–10 |
| 22 | 6 | 5 | 4.27 YR | 4.68 | 3.01 | 0.3777 | 0.3509 | 0.2717 | 17 | 12–13 |
| 5 | 7 | 6 | 3.06 YR | 5.73 | 4.62 | 0.3968 | 0.3528 | 0.2504 | 27 | 10–11 |
| 10 | 8 | 6 | 3.26 YR | 4 | 2.19 | 0.3668 | 0.3403 | 0.2929 | 12 | 17–18 |
| 44 | 9 | 7 | 2.5 YR | 4 | 2.86 | 0.3832 | 0.344 | 0.2727 | 12 | 14–15 |
| 36 | 10 | 7 | 2.47 YR | 4.68 | 3.36 | 0.3818 | 0.3464 | 0.2718 | 17 | 13–14 |
| 19 | 11 | 8 | 10 R | 4.68 | 3.71 | 0.388 | 0.3417 | 0.2708 | 17 | 15–16 |
| 17 | 12 | 8 | 10 R | 6 | 5.38 | 0.3633 | 0.3478 | 0.2889 | 30 | 16–17 |

Preparation of Triacylglycerol Oligomers Cosmetics

1. Cold Cream

| Soybean Z - 6 | 40.1% |
| Lecithin Sludge | 8.1% |
| Water | 51.8% |

2. Lotion

| Soybean Z - 3 | 30.1% |
| Lecithin Sludge | 8.1% |
| Water | 60.8% |

3. Foundation

| Soybean Z - 8 | 25.0% |
| Lecithin Sludge | 8.0% |
| Water | 57.0% |
| Pigment | 10.0% |

4. Lipstick

| Soybean Z - 10 | 40.0% |
| Lecithin | 8.0% |
| Water | 42.0% |
| Pigment | 10.0% |

5. Pucker Paint

| Soybean Z - 5 | 37.3% |
| Lecithin Sludge | 8.0% |
| Water | 44.7% |
| Pigment | 10.0% |

6. Blusher

| Soybean Z - 6 | 37.9% |
| Lecithin Sludge | 8.0% |
| Water | 44.1% |
| Pigment | 10.0% |

7. Mascara

| Soybean Z - 9 | 48.0% |
| Lecithin Sludge | 8.0% |
| Water | 34.0% |
| Carbon Black | 10.0% |

Color has three qualities which are hue, value and chroma or intensity. Hue is the quality which distinguishes one color from another, for example red or blue. It is the name of the color family. The lightness or darkness of a color is called value. We can visualize how light or how dark a color is by comparing it with a value scale showing black at the bottom and white at the top. The third dimension of color is chroma or intensity. It is often thought of as the strength or weakness of a color. We can think of intensity as the degree to which a color departs from a neutral gray of the same value.

A pleasing combination of colors is known as a color harmony. One of the greatest teachers of color harmony is nature. This phenomenon is apparent in everything that grows. Nature presents a protusion of colors, beautifully arranged and spaced is as to present a pleasing spectacle to the eye. Flowers of strong and weak colors are striking against their background. Trees in the fall of the year are never more harmonious than in their bright color schemes of red, orange, yellow, and purple against the background of clear blue sky with fading green grass and brown earth in the foreground. These colors brings a change of hues, values, and chroma, and presents a beautiful color scheme. There are four general ways to combine colors; contrast in hue, value, chroma and area. The Munsell color theory suggests three paths for color harmony. The first path is vertical with rapid changing value. We refer to this color harmony as SOPHISTICATED. The second path is lateral. This is a rapid change of hues adjacent on the color wheel. We refer to this color harmony as EXOTIC. The third path is inward.

The inward path leads to the neutral center and onto the opposite on the Munsell color wheel. We refer to this color harmony as PROVOCATIVE.

Using the color of the skin, the color of the eyes, the color of the hair and a related red a computer program was developed to produce sophisticated, exotic, and provocative color harmony schemes for skin colors shown in Table 10. The harmony schemes are set forth in Tables 11–14.

TABLE 10

Listing for Cosmetic Wardrobe Computer Program

```
1000    DIM AR(15,4), E(2)
1010    PRINT "INSERT DATA DISKETTE AND HIT 'ENTER' WHEN
        READY"
1015    INPUT ZZ
1020    GO TO 2010
1030    J = 0
1035    PRINT "INPUT HUE FACTOR FOR FOUNDATIONS" : INPUT
        BE
1040    PRINT "COLOR MATCH 1-CREAMS, 2-LIQUIDS, 3-LIQUID
        POWDERS, 4-EMULSION
1050    INPUT SE
1060    ON SE GOTO 1070, 1100, 1130, 1160, 1190
1070    DA = 6
1080    FILESPEC$ = "CREAMS"
1090    GOTO 3000
1100    DA = 9
1110    FILESPEC$ = "LIQUIDS"
1120    GOTO 3000
1130    DA = 14
1140    FILESPEC$ = "LIQPWD"
1150    GOTO 3000
1160    DA = 5
1170    FILESPEC$ = "EMULSION"
1180    GOTO 3000
1190    J = 1: BE = 5.0
1200    GOTO 2080
2010    PRINT "INPUT X-BAR"
2020    INPUT X
2030    PRINT "INPUT Y-BAR"
2040    INPUT Y
2045    PRINT "INPUT VALUE" : INPUT VV
2048    PRINT "INPUT SATURATION" : INPUT SS
2050    V1 = X − .310 : Z1 = V1
2060    V2 = Y − .316 : Z2 = V2
2062    BE = 5
2064    PRINT "INPUT NAME" : INPUT N$
2066    QQ = 1: HH = 1: LL = 1
2070    PRINT "INPUT AGE FACTOR" : INPUT FF
2075    TH = −(16 + 14/FF)
2077    GOTO 1030
2080    R = 1
2090    DA = 6
2095    FILESPEC$ = "BLUSHER"
2100    GOTO 3000
2110    R = R + 1
2112    PRINT R
2115    FILESPEC$ = "DAZZLE"
2120    DA = 9
2125    Z1 = −Z1: Z2 = −Z2
2130    GOTO 3000
2140    R = R + 1
2150    DA = 6
2155    FILESPEC$ = "NAILGLOS"
2160    GOTO 3000
2170    R = R + 1
2180    DA = 3
2190    FILESPEC$ = "LINER"
2200    GOTO 3000
2210    R = R + 1
2220    DA = 2
2225    Z1 = −Z1: Z2 = − Z2
2230    FILESPEC$ = "LIPGLOSS"
2240    GOTO 3000
3000    OPEN "I", 1, FILESPEC$
3010    FOR I = 0 TO DA
3020    INPUT#1, AR(I, 1), AR(I, 2), AR(I, 3), AR(I, 4)
3030    NEXT
```

TABLE 10-continued

Listing for Cosmetic Wardrobe Computer Program

```
3040    CLOSE 1
3045    IF J = 0 GOTO 30000
3050    ON R GOTO 40000, 30000, 30000, 30000, 30000, 30000, 30000
3060    GOTO 30000
4030    R = R + 1
4040    DA = 11
4045    FILESPEC$ = "SHADOW"
4050    GOTO 3000
4080    Y1 = AR(CW, 1) − .310
4082    Y2 = AR(CW, 2) − .316
4084    YY = SQR(Y1[2 + Y2[2)
4086    TJ = .274 − YY
4090    R = R + 1
4095    Z1 = Y1: Z2 = Y2
4100    DA = 15
4105    FILESPEC$ = "LIPSTICK"
4110    GOTO 3000
4300    GOTO 2010
30000       REM SUBROUTINE FOR CALCULATING ANGLE
            BETWEEN COLOR VECTORS
30004       LPRINT "N   E1"; TAB (34) "E2"; TAB (51) "E3"; TAB
            (63) "CO"
30005       CQ = 1000
30100       N = 0: L = 0: I = I − 1
30200       TV = SQR(Z1[2 + Z2[2)
30300       T1 = Z1/TV
30310       TT = SQR (V1[2 + V2[2)
30400       T2 = Z2/TV
30410       C1 = AR(N, 1) − .310
30420       C2 = AR(N, 2) − .316
30430       CV = SQR(C1[2 + C2[2)
30440       C3 = C1/CV
30450       C4 = C2/CV
30500       T = (T1*C3) + (T2*C4)
30510       TA = SQR(1−T[2)/T
30520       TCT = TAN(BE*. 0174533)
30550       CT = COS(BE*. 0174533)
30560       GOTO 33000
30565       CO = E1*QQ + E(1)*HH + E(2)*LL
30567       LPRINT N; " "; E1, E(1), E(2), CO
30570       IF CO>CQ GOTO 30610
30580       CQ = CO
30590       CW = N
30610       N = N + 1
30700       IF N>I GOTO 31000
30900       GOTO 30200
31000       PRINT CW
31010       LPRINT " "
31020    LPRINT "THETA", "SATURATION", "AGE FACTOR",
         FILESPEC$; " "; "NAME"
31030       LPRINT TH, TJ, FF, CW; " "; N$
31040       LPRINT " ": LPRINT " "
31045       ON SE GOTO 1040, 1040, 1040, 1035
31100       ON R GOTO 4080, 4030, 2110, 2140, 2170, 2210, 4300
31110    GOTO 4080
33000       E1 = (TCT − TA)/TCT
33010       IF E1>0 GOTO 59000
33020       E1 = −E1
33022       GOTO 59000
33040       IF E(PP)>0 GOTO 33060
33050       E(PP) = − E(PP)
33060       ON PP GOTO 65000, 30565
40000       REM SUBROUTINE FOR CALCULATING VECTOR
            COMPONENTS
40100       RR = SQR(V1[2 + V2[2)
40200       V3 = V1/RR
40210       V4 = V2/RR
40220       LE = COS(TH*. 0174533)
40230       M1 = −(2*V4*LE)
40240       M2 = 4*((V3[2 + V4[2)*(LE[2−V3[2))
40242       M3 = SQR(M1[2 − M2)
40246       F2 = ( −M1 + M3)/2*(V3[2 +V4]2)
40250       G1 = SQR(1 − F2[2)
40260       F4 = (−M1 −M3)/2*(V3[2 + V4[2)
40270       F3 = SQR(1 − F4[2)
40280       IF TH<0 GOTO 40500
40290       Z1 = G1
```

TABLE 10-continued

Listing for Cosmetic Wardrobe Computer Program

| | |
|---|---|
| 40300 | Z2 = F2 |
| 40400 | GOTO 40800 |
| 40500 | Z1 = F3 |
| 40600 | Z2 = F4 |
| 40800 | GOTO 30000 |
| 59000 | P = 3: WW = VV: PP = 1: F1 = 1 |
| 59050 | IF J = 0 GOTO 60100 |
| 60000 | ON R GOTO 60100, 60300, 61200, 60300, 60300, 61200, 60100 |
| 60100 | E(PP) = (WW − AR(N, P))/WW |
| 60200 | GOTO 33040 |
| 60300 | ON FF GOTO 60400, 60600, 60800, 61000 |
| 60400 | E(PP) = ((WW − 1. 5*F1) − AR(N, P))/( WW − 1. 5*F1) |
| 60500 | GOTO 33040 |
| 60600 | E(PP) = (( WW − 1. 0*F1) − AR(N, P))/( WW− 1. 0*F1) |
| 60700 | GOTO 33040 |
| 60800 | E(PP) = ((WW − 0. 5*F1) − AR(N, P))/(WW−0. 5*F1) |
| 60900 | GOTO 33040 |
| 61000 | E(PP) = ((WW − .25*F1) − AR(N, P))/(WW − .25*F1) |
| 61100 | GOTO 33040 |
| 61200 | ON FF GOTO 61250, 61270, 61290, 61310 |
| 61250 | E(PP) = (( WW + 1. 5*F1) − AR(N, P))//(WW +1. 5*F1) |
| 61260 | GOTO 33040 |
| 61270 | E(PP) = (( WW + 1. 0*F1) − AR(N, P))/(WW + 1. 0*F1) |
| 61280 | GOTO 33040 |
| 61290 | E(PP) = (( WW + 0. 5*F1) − AR(N, P))/( WW + .5*F1) |
| 61300 | GOTO 33040 |
| 61310 | E(PP) = (( WW + .25*F1) − AR(N, P))/( WW + .25*F1) |
| 61320 | GOTO 33040 |
| 61330 | STOP |
| 65000 | P = 4 |
| 65010 | WW = SS |
| 65020 | PP = 2 |
| 65030 | F1 = 10 |
| 65035 | IF J = 0 GOTO 60100 |
| 65040 | ON R GOTO 60100, 60300, 61200, 60300, 60300, 61200, 60100 |

LISTING FOR PROGRAM C2

| | |
|---|---|
| 1000 | DIM LPS(12, 2), BL(6, 2), ES(11, 2), AR(12, 2) |
| 1005 | R = 2 |
| 1010 | PRINT "INSERT DATA DISKETTE AND HIT 'ENTER' WHEN READY" |
| 1015 | INPUT ZZ |
| 1017 | OPEN "I", 1, "LIPSTICK" |
| 1020 | FOR I = 0 TO 12 |
| 1030 | INPUT#1, LPS(I, 1), LPS(I, 2) |
| 1040 | NEXT |
| 1050 | CLOSE 1 |
| 1060 | OPEN "I", 1, "BLUSHER" |
| 1070 | FOR I = 0 TO 6 |
| 1080 | INPUT#1, BL(I, 1), BL(I, 2) |
| 1090 | NEXT |
| 1100 | CLOSE 1 |
| 1110 | OPEN "I", 1, "SHADOW" |
| 1120 | FOR I = 0 TO 11 |
| 1130 | INPUT#1, ES(I, 1), ES(I, 2) |
| 1140 | NEXT |
| 1150 | CLOSE 1 |
| 2010 | PRINT "INPUT X-BAR" |
| 2020 | INPUT X |
| 2030 | PRINT "INPUT Y-BAR" |
| 2040 | INPUT Y |
| 2050 | V1 = X − .448: Z1 = V1 |
| 2060 | V2 = U − .408: Z2 = V2 |
| 2062 | W = 0 |
| 2064 | MLPS = 0 |
| 2066 | MBL = 0 |
| 2068 | MES = 0 |
| 4000 | REM CALCULATING FOR EXOTIC |
| 4005 | BE = 5.0 |
| 4007 | U = 1 |
| 4010 | PRINT "CALCULATING EXOTIC WARDROBE" |
| 4015 | GOTO 4140 |
| 4020 | TH = −30 |
| 4030 | GOSUB 40000 |
| 4040 | FOR I = 0 TO 11 |

TABLE 10-continued

Listing for Cosmetic Wardrobe Computer Program

| | |
|---|---|
| 4045 | AR(I, 1) = ES(I, 1) |
| 4050 | AR(I, 2) = ES(I, 2) |
| 4055 | NEXT |
| 4060 | GOSUB 30000 |
| 4070 | IF L = 0 THEN GOTO 4500 |
| 4075 | MES = N + 1 |
| 4080 | TH = 150 |
| 4090 | GOSUB 40000 |
| 4100 | FOR I = 0 TO 12 |
| 4105 | AR(I, 1) = LPS(I, 1) |
| 4110 | AR(I, 2) = LPS(I, 2) |
| 4115 | NEXT |
| 4120 | GOSUB 30000 |
| 4130 | IF L = 0 THEN GOTO 4500 |
| 4135 | MLPS = N + 1 |
| 4137 | GOSUB 10000 |
| 4138 | GOTO 5300 |
| 4140 | TH = −60 |
| 4150 | GOSUB 40000 |
| 4160 | FOR I = 0 TO 6 |
| 4165 | AR(I, 1) = BL(I, 1) |
| 4170 | AR(I, 2) = BL(I, 2) |
| 4175 | NEXT |
| 4180 | GOSUB 30000 |
| 4190 | IF L = 0 THEN GOTO 4800 |
| 4200 | MBL = N + 1 |
| 4210 | GOTO 4020 |
| 4500 | REM CALCULATING $2^{ND}$ PHASE FOR EXOTIC 1 |
| 4505 | PRINT "CALCULATING $2^{ND}$ PHASE FOR EXOTIC 1" |
| 4510 | TH = −30 |
| 4520 | GOSUB 40000 |
| 4530 | FOR I = 0 TO 12 |
| 4535 | AR(I, 1) = LPS (I, 1) |
| 4540 | AR(I, 2) = LPS (I, 2) |
| 4545 | NEXT |
| 4550 | GOSUB 30000 |
| 4560 | IF L = 0 THEN GOTO 4800 |
| 4565 | MLPS = N+1 |
| 4570 | TH = 150 |
| 4580 | GOSUB 40000 |
| 4590 | FOR I = 0 TO 6 |
| 4595 | AR(I, 1) = ES(I, 1) |
| 4600 | AR(I, 2) = ES(I, 2) |
| 4605 | NEXT |
| 4610 | GOSUB 30000 |
| 4620 | IF L = 0 THEN GOTO 4800 |
| 4630 | MES = N + 1 |
| 4640 | GOSUB 10000 |
| 4650 | GOTO 5300 |
| 4800 | REM CALCULATING FOR EX 2 WD |
| 4805 | PRINT "CALCULATING EXOTIC 2" |
| 4810 | TH = 60 |
| 4820 | GOSUB 40000 |
| 4830 | FOR I = 0 TO 6 |
| 4835 | AR(I, 1) = BL(I, 1) |
| 4840 | AR(I, 2) = BL(I, 2) |
| 4845 | NEXT |
| 4850 | GOSUB 30000 |
| 4860 | IF L = 0 THEN 5200 |
| 4870 | MBL = N + 1 |
| 4880 | TH = 30 |
| 4890 | GOSUB 40000 |
| 4900 | FOR I = 0 TO 11 |
| 4905 | AR(I, 1) = ES(I, 1) |
| 4910 | AR(I, 2) = ES(I, 2) |
| 4915 | NEXT |
| 4920 | GOSUB 30000 |
| 4930 | IF L = 0 THEN GOTO 5030 |
| 4940 | MES = N+1 |
| 4950 | TH = −150 |
| 4960 | GOSUB 40000 |
| 4970 | FOR I = 0 TO 12 |
| 4975 | AR(I, 1) = LPS(I, 1) |
| 4980 | AR(I, 2) = LPS(I, 2) |
| 4985 | NEXT |
| 4990 | GOSUB 30000 |
| 5000 | IF L = 0 THEN GOTO 5030 |

TABLE 10-continued

Listing for Cosmetic Wardrobe Computer Program

```
5010    MLPS = N + 1
5020    GOSUB 10000
5025    GOTO 5300
5030    REM CALCULATING 2ND PHASE FOR EX 2
5035    PRINT "CALCULATING 2ND PHASE FOR EXOTIC 2"
5040    TH = 30
5050    GOSUB 40000
5060    FOR I = 0 TO 12
5065    AR(I, 1) = LPS(I, 1)
5070    AR(I, 2) = LPS(I, 2)
5075    NEXT
5080    GOSUB 30000
5090    IF L = 0 THEN GOTO 5200
5100    MLPS = N + 1
5110    TH = −150
5120    GOSUB 40000
5130    FOR I = 0 TO 11
5135    AR(I, 1) = ES(I, 1)
5140    AR(I, 2) = ES(I, 2)
5145    NEXT
5150    GOSUB 30000
5160    IF L = 0 THEN GOTO 5200
5170    MES = N + 1
5180    GOSUB 10000
5190    END
5200    BE = BE + 5
5210    U = U +1
5220    PRINT "CYCLE NUMBER"; U
5230    GOTO 4140
5300    PRINT "CALCULATIONS COMPLETE FOR EXOTIC
        WARDROBE"
5310    END
10000       REM SSUBROUTINE FOR STORING COLORS
10100       MODE% = N
10200       ON R GOTO 10300, 10500, 10700
10300       FILESPEC$ = "SOPHISTICATED"
10400       GOTO 10800
10500       FILESPEC$ = "EXOTIC"
10600       GOTO 10710
10700       FILESPEC$ = PROVACATIVE
10710       PRINT "INSERT DATA DISKETTE AND HIT 'ENTER'
            WHEN READY"
10720       INPUT ZZ
10800       OPEN "O", 1, FILESPEC$
10900       PRINT#1, MLPS; MES; MBL
11000       CLOSE 1
11100       RETURN
30000       REM SUBROUTINE FOR CALCULATING ANGLE
            BETWEEN COLOR VECTORS
30100       N = 0: L = 0: I = I−1
30200       TV = SQR(Z1[2 + Z2[2)
30300       T1 = Z1/TV
30400       T2 = Z2/TV
30410       C1 = AR(N, 1) − .448
30420       C2 = AR(N, 2) − .408
30430       CV = SQR(C1[2 + C2[2)
30440       C3 = C1/CV
30450       C4 = C2/CV
30500       T = (T1*C3) + (T2*C4)
30550       CT = COS(BE* .0174533)
30600       IF T>CT THEN GOTO 31000
30610       N = N + 1
30700       IF N>I GOTO 31100
30900       GOTO 30200
31000       L = 1
31100       RETURN
40000       REM SUBROUTINE FOR CALCULATING VECTOR
            COMPPONENTS
40100       RR = SQR(V1[2 + V2[2)
40200       V3 = V1/RR
40210       V4 = V2/RR
40220       LE = COS(TH* .0174533)
40230       M1 = −(2*V4*LE)
40240       M2 = 4*((V3[2 +V4[2)*(LE[2−V3[2))
40242       M3 = SQR(M1[2 − M2)/2*(V3[2+V4[2)
40246       F2 = −M1 + M3
40250       F1 = SQR(1 − F2[2)
40260       F4 = −M1 −M3
40270       F3 = SQR(1 − F4[2)
40280       IF TH<0 GOTO 40500
40290       Z1 = F1
40300       Z2 = F2
40400       GOTO 40800
40500       Z1 = F3
40600       Z2 = F4
40800       RETURN
            LISTING FOR PROGRAM C3
1000    DIM AR(15, 4), E(2)
1010    PRINT "INSERT DATA DISKETTE AND HIT 'ENTER' WHEN
        READY"
1015    INPUT ZZ
1020    GOTO 2010
1030    J = 0
1035    PRINT "INPUT HUE FACTOR FOR FOUNDATIONS" : INPUT
        BE
1040    PRINT "COLOR MATCH 1-CREAMS, 2-LIQUIDS, 3-LIQUID
        POWDERS, 4-EMULSION
1050    INPUT SE
1060    ON SE GOTO 1070, 1100, 1130, 1160, 1190
1070    DA = 6
1080    FILESPEC$ = "CREAMS"
1090    GOTO 3000
1100    DA = 9
1110    FILESPEC$ = "LIQUIDS"
1120    GOTO 3000
1130    DA = 14
1140    FILESPEC$ = "LIQPWD"
1150    GOTO 3000
1160    DA = 5
1170    FILESPEC$ = "EMULSION"
1180    GOTO 3000
1190    J = 1: BE = 5.0
1200    GOTO 2080
2010    PRINT "INPUT X-BAR"
2020    INPUT X
2030    PRINT "INPUT Y-BAR"
2040    INPUT Y
2045    PRINT "INPUT VALUE": INPUT VV
2048    PRINT "INPUT SATURATION": INPUT SS
2050    V1 = X − .310 : Z1 = V1
2060    V2 = Y − .316 : Z2 = V2
2062    BE = 5
2064    PRINT "INPUT NAME": INPUT N$
2066    QQ = 1: HH = 1: LL = 1
2070    PRINT "INPUT AGE FACTOR": INPUT FF
2075    TH = −(16 + 14/FF)
2077    GOTO 1030
2080    R = 1
2090    DA = 6
2095    FILESPEC$ = "BLUSHER"
2100    GOTO 3000
2110    R = R + 1
2112    PRINT R
2115    FILESPEC$ = "DAZZLE"
2120    DA = 9
2125    Z1 = −Z1: Z2 = −Z2
2130    GOTO 3000
2140    R = R +1
2150    DA = 6
2155    FILESPEC$ = "NAILGLOS"
2160    GOTO 3000
2170    R = R + 1
2180    DA = 3
2190    FILESPEC$ = "LINER"
2200    GOTO 3000
2210    R = R + 1
2220    DA = 2
2225    Z1 = −Z1: Z2 = −Z2
2230    FILESPEC$ = "LIPGLOSS"
2240    GOTO 3000
3000    OPEN "I", 1, FILESPEC$
3010    FOR I = 0 TO DA
3020    INPUT#1, AR(I, 1), AR(I, 2), AR(I, 3), AR(I, 4)
```

TABLE 10-continued

Listing for Cosmetic Wardrobe Computer Program

| | |
|---|---|
| 3030 | NEXT |
| 3040 | CLOSE 1 |
| 3045 | IF J = 0 GOTO 30000 |
| 3050 | ON R GOTO 40000, 30000, 30000, 30000, 30000, 30000, 30000 |
| 3060 | GOTO 30000 |
| 4030 | R = R + 1 |
| 4040 | DA = 11 |
| 4045 | FILESPEC$ = "SHADOW" |
| 4050 | GOTO 3000 |
| 4080 | Y1 = AR(CW, 1) − .310 |
| 4082 | Y2 = AR(CW, 2) − .316 |
| 4084 | YY = SQR(Y1[2 + Y2[2) |
| 4086 | TJ = .274 − YY |
| 4090 | R = R + 1 |
| 4095 | Z1 = Y1: Z2 = Y2 |
| 4100 | DA = 15 |
| 4105 | FILESPEC$ = "LIPSTICK" |
| 4110 | GOTO 3000 |
| 4300 | GOTO 2010 |
| 30000 | REM SUBROUTINE FOR CALCULATING ANGLE BETWEEN COLOR VECTORS |
| 30004 | PRINT "N   E1"; TAB(34) "E2"; TAB (51) "E3"; TAB (63) "CO" |
| 30005 | CQ = 1000 |
| 30100 | N = 0: L = 0: I = I − 1 |
| 30200 | TV = SQR(Z1[2 + Z2[2) |
| 30300 | T1 = Z1/TV |
| 30310 | TT = SQR(V1[2 +V2[2) |
| 30400 | T2 = Z2/TV |
| 30410 | C1 = AR(N, 1) − .310 |
| 30420 | C2 = AR(N, 2) − .316 |
| 30430 | CV = SQR(C1[2 + C2[2) |
| 30440 | C3 = C1/CV |
| 30450 | C4 = C2/CV |
| 30500 | T = (T1*C3) + (T2*C4) |
| 30510 | TA = SQR(1 − T[2)/T |
| 30520 | TCT = TAN (BE* .0174533) |
| 30550 | CT = COS(BE* .0174533) |
| 30560 | GOTO 33000 |
| 30565 | CO + E1*QQ +(1)*HH + E(2)*LL |
| 30567 | PRINT N; " "; E1, E(1), E(2), CO |
| 30570 | IF CO>CQ GOTO 30610 |
| 30580 | CQ = CO |
| 30590 | CW = N |
| 30610 | N = N + 1 |
| 30700 | IF N>I GOTO 31000 |
| 30900 | GOTO 30200 |
| 31000 | PRINT CW |
| 31010 | PRINT " " |
| 31020 | PRINT "THETA", "SATURATION", "AGE FACTOR", FILESPEC$; " "; "NAME" |
| 31030 | PRINT TH, TJ, FF, CW; " "; N$ |
| 31045 | ON SE GOTO 1040, 1040, 1040, 1035 |
| 31100 | ON R GOTO 4080, 4030, 2110, 2140, 2170, 2210, 4300 |
| 31110 | GOTO 4080 |
| 33000 | E1 = (TCT − TA)/TCT |
| 33010 | IF E1>0 GOTO 59000 |
| 33020 | E1 = −E1 |
| 33022 | GOTO 59000 |
| 33040 | IF E(PP) > 0 GOTO 33060 |
| 33050 | E(PP) = − E(PP) |
| 33060 | ON PP GOTO 65000, 30565 |
| 40000 | REM SUBROUTINE FOR CALCULATING VECTOR COMPONENTS |
| 40100 | RR = SQR (V1[2 + V2[2) |
| 40200 | V3 = V1/RR |
| 40210 | V4 = V2/RR |
| 40220 | LE = COS(TH* .0174533) |
| 40230 | M1 = −(2*V4*LE) |
| 40240 | M2 = 4*((V3[2 + V4[2)*(LE[2−V3[2)) |
| 40242 | M3 = SQR(M1[2 −M2) |
| 40246 | F2 = ( −M1 + M3)/2*(V3[2 +V4[2) |
| 40250 | G1 = SQR(1 − F2[2) |
| 40260 | F4 = (−M1 −M3)/2*(V3[2 +V4[2) |
| 40270 | F3 = SQR(1 − F4[2) |
| 40280 | IF TH<0 GOTO 40500 |
| 40290 | Z1 = G1 |
| 40300 | Z2 = F2 |
| 40400 | GOTO 40800 |
| 40500 | Z1 = F3 |
| 40600 | Z2 = F4 |
| 40800 | GOTO 30000 |
| 59000 | P = 3: WW = VV: PP = 1: F1 = 1 |
| 59050 | IF J = 0 GOTO 60100 |
| 60000 | ON R GOTO 60100, 60300, 61200, 60300, 60300, 61200, 60100 |
| 60100 | E(PP) = (WW − AR(N, P))/WW |
| 60200 | GOTO 33040 |
| 60300 | ON FF GOTO 60400, 60600, 60800, 61000 |
| 60400 | E(PP) = ((WW − 1.5*F1) − AR(N, P))/(WW − 1.5*F1) |
| 60500 | GOTO 33040 |
| 60600 | E(PP) = ((WW − 1.0*F1) − AR(N, P))/(WW − 1.0*F1) |
| 60700 | GOTO 33040 |
| 60800 | E(PP) = ((WW − 0.5*F1) − AR(N, P))/(WW − 0.5*F1) |
| 60900 | GOTO 33040 |
| 61000 | E(PP) = ((WW − .25*F1) − AR(N, P))/(WW − .25*F1) |
| 60200 | GOTO 33040 |
| 60300 | ON FF GOTO 60400, 60600, 60800, 61000 |
| 60400 | E(PP) = ((WW − 1.5*F1) − AR(N, P))/(WW − 1.5*F1) |
| 60500 | GOTO 33040 |
| 60600 | E(PP) = ((WW − 1.0*F1) − AR(N, P))/(WW − 1.0*F1) |
| 60700 | GOTO 33040 |
| 60800 | E(PP) = ((WW − 0.5*F1) − AR(N, P))/(WW − 0.5*F1) |
| 60900 | GOTO 33040 |
| 61000 | E(PP) = ((WW −.25*F1) − AR(N, P))/(WW − .25*F1) |
| 61100 | GOTO 33040 |
| 61200 | ON FF GOTO 61250, 61270, 61290, 61310 |
| 61250 | E(PP) = ((WW + 1.5*F1) − AR(N, P))/(WW + 1.5*F1) |
| 61260 | GOTO 33040 |
| 61270 | E(PP) = ((WW + 1.0*F1) − AR(N, P))/(WW + 1.0*F1) |
| 61280 | GOTO 33040 |
| 61290 | E(PP) = ((WW + 0.5*F1) − AR(N, P))/(WW + 0.5*F1) |
| 61300 | GOTO 33040 |
| 61310 | E(PP) = ((WW + .25*F1) − AR(N, P))/(WW + .25*F1) |
| 61320 | GOTO 33040 |
| 61330 | STOP |
| 65000 | P = 4 |
| 65010 | WW = SS |
| 65020 | PP = 2 |
| 65030 | F1 = 10 |
| 65035 | IF J = 0 GOTO 60100 |
| 65040 | ON R GOTO 60100, 60300, 61200, 60300, 60300, 61200, 60100 |

LISTING FOR PROGRAM C1

| | |
|---|---|
| 1000 | DIM AR(15,4), E(2) |
| 1010 | PRINT "INSERT DATA DISKETTE AND HIT 'ENTER' WHEN READY" |
| 1015 | INPUT ZZ |
| 1020 | GO TO 2010 |
| 1030 | J = 0 |
| 1035 | PRINT "INPUT HUE FACTOR FOR FOUNDATIONS" : INPUT BE |
| 1040 | PRINT "COLOR MATCH 1-CREAMS, 2-LIQUIDS, 3-LIQUID POWDERS, 4-EMULSION |
| 1050 | INPUT SE |
| 1060 | ON SE GOTO 1070, 1100, 1130, 1160, 1190 |
| 1070 | DA = 6 |
| 1080 | FILESPEC$ = "CREAMS" |
| 1090 | GOTO 3000 |
| 1100 | DA = 9 |
| 1110 | FILESPEC$ = "LIQUIDS" |
| 1120 | GOTO 3000 |
| 1130 | DA = 14 |
| 1140 | FILESPEC$ = "LIQPWD" |
| 1150 | GOTO 3000 |
| 1160 | DA = 5 |
| 1170 | FILESPEC$ = "EMULSION" |
| 1180 | GOTO 3000 |
| 1190 | J = 1: BE = 5.0 |
| 1200 | GOTO 2080 |
| 2010 | PRINT "INPUT X-BAR" |
| 2020 | INPUT X |
| 2030 | PRINT "INPUT Y-BAR" |

TABLE 10-continued

Listing for Cosmetic Wardrobe Computer Program

```
2040   INPUT Y
2045   PRINT "INPUT VALUE" : INPUT VV
2048   PRINT "INPUT SATURATION" : INPUT SS
2050   V1 = X − .310 : Z1 = V1
2060   V2 = Y − .316 : Z2 = V2
2062   BE = 5
2064   PRINT "INPUT NAME" : INPUT N$
2066   QQ = 1: HH = 1: LL = 1
2070   PRINT "INPUT AGE FACTOR" : INPUT FF
2075   TH = −(16 + 14/FF)
2077   GOTO 1030
2080   R = 1
2090   DA = 6
2095   FILESPEC$ = "BLUSHER"
2100   GOTO 3000
2110   R = R + 1
2112   PRINT R
2115   FILESPEC$ = "DAZZLE"
2120   DA = 9
2125   Z1 = −Z1: Z2 = −Z2
2130   GOTO 3000
2140   R = R + 1
2150   DA = 6
2155   FILESPEC$ = "NAILGLOS"
2160   GOTO 3000
2170   R = R + 1
2180   DA = 3
2190   FILESPEC$ = "LINER"
2200   GOTO 3000
2210   R = R + 1
2220   DA = 2
2225   Z1 = −Z1: Z2 = − Z2
2230   FILESPEC$ = "LIPGLOSS"
2240   GOTO 3000
3000   OPEN "I", 1, FILESPEC$
3010   FOR I = 0 TO DA
3020   INPUT#1, AR(I, 1), AR(I, 2), AR(I, 3), AR(I, 4)
3030   NEXT
3040   CLOSE 1
3045   IF J = 0 GOTO 30000
3050   ON R GOTO 40000, 30000, 30000, 30000, 30000, 30000, 30000
3060   GOTO 30000
4030   R = R + 1
4040   DA = 11
4045   FILESPEC$ = "SHADOW"
4050   GOTO 3000
4080   Y1 = AR(CW, 1) − .310
4082   Y2 = AR(CW, 2) − .316
4084   YY = SQR(Y1[2 + Y2[2)
4086   TJ = .274 − YY
4090   R = R + 1
4095   Z1 = Y1: Z2 = Y2
4100   DA = 15
4105   FILESPEC$ = "LIPSTICK"
4110   GOTO 3000
4300   GOTO 2010
30000        REM SUBROUTINE FOR CALCULATING ANGLE
             BETWEEN COLOR VECTORS
30004        PRINT "N   E1"; TAB (34) "E2"; TAB (51) "E3"; TAB
             (63) "CO"
30005        CQ = 1000
30100        N = 0: L = 0: I = I − 1
30200        TV = SQR(Z1[2 + Z2[2)
30300        T1 = Z1/TV
30310      TT = SQR (V1[2 + V2[2)
30400        T2 = Z2/TV
30410        C1 = AR(N, 1) − .310
30420        C2 = AR(N, 2) − .316
30430        CV = SQR(C1[2 + C2[2)
30440        C3 = C1/CV
30450        C4 = C2/CV
30500        T = (T1*C3) + (T2*C4)
30510        TA = SQR(1−T[2)/T
30520        TCT = TAN(BE*. 0174533)
30550        CT = COS(BE*. 0174533)
30560     GOTO 33000
30565        CO = E1*QQ + E(1)*HH + E(2)*LL
30567        PRINT N; " "; E1, E(1), E(2), CO
30570        IF CO>CQ GOTO 30610
30580        CQ = CO
30590        CW = N
30610        N = N +1
30700        IF N>I GOTO 31000
30900        GOTO 30200
31000        PRINT CW
31010        PRINT " "
31020   PRINT "THETA", "SATURATION", "AGE FACTOR",
        FILESPEC$; " "; "NAME"
31030        PRINT TH, TJ, FF, CW; " "; N$
31045        ON SE GOTO 1040, 1040, 1040, 1035
31100        ON R GOTO 4080, 4030, 2110, 2140, 2170, 2210, 4300
31110   GOTO 4080
33000        E1 = (TCT − TA)/TCT
33010        IF E1>0 GOTO 59000
33020        E1 = −E1
33022        GOTO 59000
33040        IF E(PP)>0 GOTO 33060
33050        E(PP) = − E(PP)
33060        ON PP GOTO 65000, 30565
40000        REM SUBROUTINE FOR CALCULATING VECTOR
             COMPONENTS
40100        RR = SQR(V1[2 + V2[2)
40200        V3 = V1/RR
40210        V4 = V2/RR
40220        LE = COS(TH*. 0174533)
40230        M1 = −(2*V4*LE)
40240        M2 = 4*((V3[2 + V4[2)*(LE[2−V3[2))
40242        M3 = SQR(M1[2 − M2)
40246        F2 = ( −M1 + M3)/2*(V3[2 +V4]2)
40250        G1 = SQR(1 − F2[2)
40260        F4 = (−M1 −M3)/2*(V3[2 + V4[2)
40270        F3 = SQR(1 − F4[2)
40280        IF TH<0 GOTO 40500
40290        Z1 = G1
40300        Z2 = F2
40400        GOTO 40800
40500        Z1 = F3
40600        Z2 = F4
40800        GOTO 30000
59000        P = 3: WW = VV: PP = 1: F1 = 1
59050        IF J = 0 GOTO 60100
60000        ON R GOTO 60100, 60300, 61200, 60300, 60300, 61200,
             60100
60100   E(PP) = (WW − AR(N, P))/WW
60200   GOTO 33040
60300        ON FF GOTO 60400, 60600, 60800, 61000
60400        E(PP) = ((WW − 1. 5*F1) − AR(N, P))/( WW − 1. 5*F1)
60500   GOTO 33040
60600        E(PP) = (( WW − 1. 0*F1) − AR(N, P))/( WW− 1. 0*F1)
60700        GOTO 33040
60800        E(PP) = ((WW − 0. 5*F1) − AR(N, P))/(WW−0. 5*F1)
60900        GOTO 33040
61000        E(PP) = ((WW − .25*F1) − AR(N, P))/(WW − .25*F1)
61100        GOTO 33040
61200   ON FF GOTO 61250, 61270, 61290, 61310
61250        E(PP) = (( WW + 1. 5*F1) − AR(N, P))//(WW +1. 5*F1)
61260        GOTO 33040
61270        E(PP) = (( WW + 1. 0*F1) − AR(N, P))/(WW + 1. 0*F1)
61280        GOTO 33040
61290        E(PP) = (( WW + 0. 5*F1) − AR(N, P))/( WW + .5*F1)
61300        GOTO 33040
61310        E(PP) = (( WW + .25*F1) − AR(N, P))/( WW + .25*F1)
61320        GOTO 33040
61330        STOP
65000        P = 4
65010        WW = SS
65020        PP = 2
65030        F1 = 10
65035        IF J = 0 GOTO 60100
65040        ON R GOTO 60100, 60300, 61200, 60300, 60300, 61200,
             60100
```

TABLE 10-continued

Listing for Cosmetic Wardrobe Computer Program

LISTING FOR PROGRAM COLORS

```
2000  DIM LPS (I, K), BL(I, K), ES(I, K)
2010  PRINT "INPUT X-BAR"
2020  INPUT X
2030  PRINT "INPUT Y-BAR"
2040  INPUT Y
2045  CT = .99619
2050  V1 = X − .448
2060  V2 = Y − .408
2061  R = 0
2062  W = 0
2064  MLPS = 0
2066  MBL = 0
2068  MES = 0
2070  Z1 = −V1
2080  Z2 = −V2
2090  R = R + 1
2092  W = W + 1
2095  IF MLPS>0 GOTO 2165
2100  PRINT "CALCULATING COLOR FOR LPS FOR PHASE" ; R
2110  AR(N, I) = LPS(I, K)
2120  I = 15
2130  GOSUB 30000
2140  IF L = 0 THEN GOTO 2165
2150  MLPS = N + 1
2160  ON W GOTO 2300, 2600, 2600, 2600, 2600
2165  IF MBL>0 GOTO 2235
2170  PRINT "CALCULATING COLOR USING BL FOR PHASE"; R
2180  I = 8
2190  AR(N, J) = BL(I, K)
2200  GOSUB 30000
2210  IF L = 0 THEN GOTO 2235
2220  MBL = N + 1
2230  ON W GOTO 2320, 2600, 2600, 2600, 2600
2235  IF MES>0 THEN GOTO 2600
2240  PRINT "CALCULATING COLOR FOR ES FOR PHASE" ; R
2250  I = 20
2260  AR(N, J) = ES(I, K)
2270  GOSUB 30000
2280  IF L = 0 THEN GOTO 4000
2290  MESS = N +1
2295  ON W GOTO 2340, 2600, 2600, 2600, 2600
2300  P = 1
2310  GOTO 2600
2320  P = 2
2330  GOTO 2600
2340  P = 3
2350  GOTO 2600
2600  REM CALCULATING ACCENTS
2620  PRINT "CALCULATION OF COLOR FOR 1ST ACCENT FOR PHASE 1"
2640  ON W GOTO 2650, 2680, 2700, 2930, 2960
2650  TH = 30
2660  GOSUB 40000
2670  GOTO 2092
2680  TH = −30
2690  GOSUB 40000
2695  GOTO 2092
2700  IF MLPS = 0 THEN GOTO 2800
2710  IF MBL = 0 THEN GOTO 2800
2720  IF MES = 0 THEN GOTO 2800
2730  GOSUB 10000
2740  GOTO 4000
2800  REM CALCULATING COLORS FOR 2ND ACCENT FOR PHASE 1
2805  PRINT "CALCULATING COLORS FOR 2ND ACCENT FOR PHASE" ; R
2810  ON P GOTO 2820, 2850, 2880
2820  MBL = 0
2830  MES = 0
2840  GOTO 2900
2850  MLPS = 0
2860  MES = 0
2870  GOTO 2900
2880  MLPS = 0
2890  MBL = 0
2900  TH = 60
2910  GOSUB 40000
2920  GOTO 2092
2930  TH = −60
2940  GOSUB 40000
2950  GOTO 2092
2960  IF MLPS = 0 THEN GOTO 3000
2970  IF MBL = 0 THEN GOTO 3000
2980  IF MES = 0 THEN GOTO 3000
2990  GOSUB 10000
2995  GOTO 4000
3000  PRINT "INCREASE COSINE THETA AND RECYCLE" : LINEINPUT CT
3010  GOTO 2050
4000  REM CALCULATING FOR EXOTIC
4005  CT = .99619
4010  PRINT "CALCULATING EXOTIC WARDROBE"
4015  GOTO 4140
4020  TH = −30
4030  GOSUB 40000
4040  I = 20
4050  AR(N, J) = ES(I, K)
4060  GOSUB 30000
4070  IF L = 0 THEN GOTO 4500
4075  MES = N
4080  TH = 150
4090  GOSUB 40000
4100  I = 12
4110  AR(N, I) = LPS(I, K)
4120  GOSUB 30000
4130  IF L = 0 THEN GOTO 4500
4135  MLPS = N
4137  GOSUB 10000
4138  GOTO 6000
4140  TH = −60
4150  GOSUB 40000
4160  I = 5
4170  AR(N, J) = BL(I, K)
4180  GOSUB 30000
4190  IF L = 0 THEN GOTO 4800
4200  MBL = N
4210  GOTO 4020
4500  REM CALCULATING 2ND PHASE FOR EXOTIC 1
4505  PRINT "CALCULATING 2ND PHASE FOR EXOTIC 1"
4510  TH = −30
4520  GOSUB 40000
4530  I = 5
4540  AR(N, I) = LPS(I, K)
4550  GOSUB 30000
4560  IF L = 0 THEN GOTO 4800
4565  MLPS = N
4570  TH = 150
4580  GOSUB 40000
4590  I = 5
4600  AR(N, J) = ES(I, K)
4610  GOSUB 30000
4620  IF L = 0 THEN GOTO 4800
4630  MES = N
4640  GOSUB 10000
4650  GOTO 6000
4800  REM CALCULATING FOR EX 2 WD
4810  TH = 60
4820  GOSUB 40000
4830  I = 5
4840  AR(N, J) = BL(I, K)
4850  GOSUB 30000
4860  IF L = 0 THEN 5200
4870  MBL = N
4880  TH = 30
4890  GOSUB 40000
4900  I = 5
4910  AR(N, J) = ES(I, K)
4920  GOSUB 30000
4930  IF L = 0 THEN GOTO 5030
4940  MES = N
4950  TH = −150
4960  GOSUB 40000
```

TABLE 10-continued

Listing for Cosmetic Wardrobe Computer Program

```
4970    I = 5
4980    AR(N, I) = LPS(I, K)
4990    GOSUB 30000
5000    IF L = 0 THEN GOTO 5030
5010    MLPS = N
5020    GOSUB 10000
5025    GOTO 6000
5030    REM CALCULATING 2ND PHASE FOR EX 2
5040    TH = 30
5050    GOSUB 40000
5060    I = 5
5070    AR(N, I) = LPS(I, K)
5080    GOSUB 30000
5090    IF L = 0 THEN GOTO 5200
5100    MLPS = N
5110    TH = -150
5120    GOSUB 40000
5130    I = 5
5140    AR(N, J) = ES(I, K)
5150    GOSUB 30000
5160    IF L = 0 THEN GOTO 5200
5170    MES = N
5180    GOSUB 10000
5190    GOTO 6000
5200    PRINT "INCREASE COSINE THETA AND RECYCLE" :
        LINEINPUT CT
5210    GOTO 4010
6000    REM CALCULATIONF FOR PROVACATIVE
6010    CT = .99619
6015    R = 3
6020    PRINT "CALCULATING FIRST STAGE OF PROVACATIVE"
6030    TH = -120
6040    GOSUB 40000
6050    I = 5
6060    AR(N, J) = BL(I, K)
6070    GOSUB 30000
6080    IF L = 0 THEN GOTO 6400
6090    MBL = 0
6100    TH = -60
6110    GOSUB 40000
6120    I = 5
6130    AR(N, J) = ES(I, K)
6140    GOSUB 30000
6150    IF L = 0 THEN GOTO 6250
6160    MES = N
6170    TH = 120
6180    GOSUB 40000
6190    I = 5
6200    AR(N, J) = LPS(I, K)
6210    GOSUB 30000
6220    L = 0 THEN GOTO 6250
6230    MLPS = N
6240    GOSUB 10000
6245    GOTO 7000
6250    GOSUB 40000
6270    I = 5
6280    AR(N, I) = LPS(I, K)
6290    GOSUB 30000
6300    IF L = 0 THEN GOTO 6400
6310    MLPS = N
6320    TH = 120
6330    GOSUB 40000
6340    I = 5
6350    AR(N, J) = ES(I, K)
6360    GOSUB 30000
6370    IF L = 0 THEN GOTO 6400
6380    MES = N
6390    GOSUB 10000
6395    GOTO 7000
6400    REM CALCULATING SECOND PHASE OF PROVACATIVE
6410    PRINT "CALCULATING SECOND PHASE OF
        PROVACATIVE"
6420    TH = 120
6430    GOSUB 40000
6440    I = 5
6450    AR(N, J) = BL(I, K)
6460    GOSUB 30000
6470    MBL = N
6490    TH = 60
6500    GOSUB 40000
6510    I = 5
6520    AR(N, J) = LPS (I, K)
6530    GOSUB 30000
6540    IF L = 0 THEN GOTO 6700
6550    MLPS = N
6560    TH = -120
6570    GOSUB 40000
6580    I = 5
6590    AR(N, J) = ES(I, K)
6600    GOSUB 30000
6610    IF L = 0 THEN GOTO 6700
6620    MES = N
6630    GOSUB 10000
6640    GOTO 7000
6700    TH = 60
6710    GOSUB 40000
6720    I = 5
6730    AR(N, J) = ES(I, K)
6740    GOSUB 30000
6750    IF L = 0 THEN GOTO 6850
6760    MES = N
6770    TH = -120
6780    GOSUB 40000
6790    I = 5
6800    AR(N, J) = LPS(I, K)
6810    GOSUB 30000
6820    IF L = 0 THEN GOTO 6850
6830    MLPS = N
6840    GOSUB 10000
6845    GOTO 7000
6850    PRINT "INCREASE COSINE THETA AND RECYCLE" :
        LINEINPUT CT
6860    GOTO 4010
7000    END
10000   REM SSUBROUTINE FOR STORING COLORS
10100   MODE% = N
10200   ON R GOTO 10300, 10500, 10700
10300   FILESPEC$ = SOPHISTICATED
10400   GOTO 10800
10500   FILESPEC$ = EXOTIC
10600   GOTO 10800
10700   FILESPEC$ = PROVACATIVE
10800   OPEN "O", MODE%, FILESPEC$
10900   PRINT#MODE%, MLPS; MES; MBL
11000   CLOSE MODE%
11100   RETURN
30000   REM SUBROUTINE FOR CALCULATING ANGLE
        BETWEEN COLOR VECTORS
30100   N = 0: L = 0
30200   TV = SQR(Z1[2 + Z2[2)
30300   CV = SQR(AR(N, 1)[2 + AR(N, 2)[2)
30400   DP = (V1*AR(N, 1) + (V2*AR(N, 2))
30500   T = DP/(TV*CV)
30600   IF T<CT THEN GOTO 31000
30700   IF N>I GOTO 31100
30800   N = N + 1
30900   GOTO 30200
31000   L = 1
31100   RETURN
40000   REM SUBROUTINE FOR CALCULATING VECTOR
        COMPONENTS
40100   RR = SQR(V1[2 + V2[2)
40200   BB = (V1*COS(TH* .0174533) + V2*SIN(TH*
        0.174533))
40300   AA = SQR(RR[2 - BB[2)
40400   Z1 = BB
40500   Z2 = AA
40600   RETURN
            LISTING FOR PROGRAM WARDROBE
5       CLEAR 1000
10      PRINT "NAME ?" : LINEINPUT NM$
15      PRINT NM$
20      PRINT "HAIR ?" : LINEINPUT H11$: INPUT H22$:
```

TABLE 10-continued

Listing for Cosmetic Wardrobe Computer Program

| | |
|---|---|
| | LINEINPUT H33$ |
| 25 | PRINT H11$, H22$, H33$ |
| 30 | PRINT "EYES ?" : LINEINPUT E11$: LINEINPUT E22$: LINEINPUT E33$ |
| 35 | PRINT E11$, E22$, E33$ |
| 40 | PRINT "SKIN ?" : LINEINPUT S11$: LINEINPUT S22$: LINEINPUT S33$ |
| 45 | PRINT S11$, S22$, S33$ |
| 50 | PRINT "RED ?" : LINEINPUT R11$: LINEINPUT R22$: LINEINPUT R33$ |
| 55 | PRINT R11$, R22$, R33$ |
| 60 | PRINT "COLOR CODE ?" : LINEINPUT CC$ |
| 65 | PRINT CC$ |
| 70 | PRINT "COLOR DIFF ?" : LINEINPUT CD$ |
| 75 | PRINT CD$ |
| 80 | PRINT "SKIN CARE ?" : LINE INPUT SC$ |
| 85 | PRINT SC$ |
| 90 | PRINT "CLEANSER ?" : LINEINPUT CL$ |
| 95 | PRINT CL$ |
| 100 | PRINT "ASTRINGENT/TONER ?" : LINEINPUT AT$ |
| 105 | PRINT AT$ |
| 110 | PRINT "MOISTURIZER ?" : LINEINPUT MT$ |
| 115 | PRINT MT$ |
| 120 | PRINT "FOUNDATION ?" : LINEINPUT FD$ |
| 125 | PRINT FD$ |
| 130 | PRINT "POWDER ?" : LINEINPUT PD$ |
| 135 | PRINT PD$ |
| 140 | PRINT "BLUSHER ?" : LINEINPUT BL$ |
| 145 | PRINT BL$ |
| 150 | PRINT "LIQUID LINER ?" : LINEINPUT LL$ |
| 155 | PRINT LL$ |
| 160 | PRINT "MASCARA ?" : LINEINPUT MAS$ |
| 165 | PRINT MAS$ |
| 170 | PRINT "LIPSTICK ?" : LINEINPUT LPS$ |
| 175 | PRINT LPS$ |
| 180 | PRINT "LIP GLOSS ?" : LINEINPUT LG$ |
| 185 | PRINT LG$ |
| 190 | PRINT "NAIL GLOSS ?" : LINEINPUT NG$ |
| 195 | PRINT NG$ |
| 200 | PRINT "GLAMOUR ITEMS ?" : LINEINPUT DZ$: LINEINPUT PP$ : |
| 205 | PRINT DZ$, PP$ |
| 207 | PRINT "EYE SHADOW ?" : LINEINPUT SW$ |
| 209 | PRINT SW$ |
| 210 | PRINT "ACCESSORIES ?" : LINE INPUT SA$: LINEINPUT PFB$: LINEINPUT LB$ |
| 212 | PRINT "COLOR STICK ?" : LINEINPUT CK$ |
| 214 | PRINT CK$ |
| 215 | PRINT SA$, PFB$, LB$ |
| 216 | PRINT "EYE DISGUISE ?" : LINEINPUT DS$ |
| 400 | REM PRINTING RESULTS OF ANALYSIS |
| 410 | LPRINT TAB(16) "EBBTONE COMPOSITE PERSONAL COLOR HARMONY" |
| 420 | LPRINT " " |
| 430 | LPRINT TAB(35) "FOR" : LPRINT " " |
| 440 | LPRINT TAB(30) NM$: LPRINT " " |
| 450 | LPRINT "YOU ARE BORN WITH A COLOR COMBINATION THAT HAS COMPLETE IND: |
| 460 | LPRINT "AND BEAUTY IN ITS HARMONY. THE COLORS OF YOUR SKIN, HAIR, EYES |
| 470 | LPRINT "RELATED RED FORM WHAT WE CALL YOUR COMPOSITE PERSONAL COLOR |
| 480 | LPRINT "BASED ON THE RESULTS FROM THE EBBTONE PROCESS, YOUR COMPOSI |
| 490 | LPRINT "COLOR HARMONY IS GIVEN BELOW IN THE THREE DIMENSIONS OF COLOR |
| 500 | LPRINT " ": LPRINT " " |
| 510 | LPRINT " ", "HUE", "VALUE", "CHROMA" |
| 520 | LPRINT "COLOR OF HAIR", H11$, H22$, H33$ |
| 530 | LPRINT "COLOR OF EYES", E11$, E22$, E33$ |
| 540 | LPRINT "COLOR OF SKIN", S11$, S22$, S33$ |
| 550 | LPRINT "RELATED RED", R11$, R22$, R33$ |
| 560 | LPRINT"--------------------------------------------------------------------" |
| 620 | LPRINT " " |
| 640 | LPRINT TAB(17) "YOUR EBBTONE PERSONALIZED COSMETIC WARDROBE" |
| 650 | LPRINT " " |
| 660 | LPRINT "THE THEME FOR YOUR EBBTONE PERSONALIZED COSMETIC WARDROBE CO |
| 670 | LPRINT "DETERMINED USING YOUR COMPOSITE PERSONAL COLOR HARMONY. YOUR |
| 680 | LPRINT "COSMETIC WARDROBE COLORS WILL EXPRESS, INTERPRET, AND EXTEND |
| 690 | LPRINT "PERSONAL COLOR THEME." |
| 700 | LPRINT " " |
| 720 | LPRINT "YOUR COLOR CODE IS" ; " " ; CC$ |
| 730 | LPRINT " " |
| 740 | LPRINT "YOUR COLOR DIFFERENCE IS" ; " " ; CD$ |
| 760 | LPRINT " " |
| 780 | LPRINT "SKIN CARE" ; " " ; SC$, "CLEANSER" ; " " ; CL$ |
| 785 | LPRINT " " |
| 790 | LPRINT "MOISTURIZER" ; " " ; MT$, "FOUNDATION" ; " " ; FD$ |
| 795 | LPRINT " " |
| 800 | LPRINT "POWDER" ; " " ; PD$, "BLUSHER" ; " " ; BL$ |
| 805 | LPRINT " " |
| 810 | LPRINT "LIQUID LINER" ; " " ; LL$, "MASCARA" ; " " MAS$ |
| 815 | LPRINT " " |
| 820 | LPRINT "LIPSTICK" ; " " ; LPS$, "LIPGLOSS" ; " " ; LG$ |
| 825 | LPRINT " " |
| 830 | LPRINT "NAIL GLOSS" ; " " ; NG$, "ASTRINGENT/TONER" ; " " AT$ |
| 835 | LPRINT " " |
| 840 | LPRINT "DAZZLE DUST" ; " " DZ$, "PUCKER PAINT" ; " " ; PP$ |
| 845 | LPRINT " " |
| 847 | LPRINT "EYE SHADOW" ; " " SW$, "COLOR STICK" ; " " ; CK$ |
| 848 | LPRINT " " |
| 850 | LPRINT SA$, PFB$, LB$, DS$ |

LISTING FOR PROGRAM SOPHISTI

| | |
|---|---|
| 5 | CLEAR 1000 |
| 10 | PRINT "NAME ?" ; LINEINPUT NM$ |
| 15 | PRINT NM$ |
| 20 | PRINT "HAIR ?" ; LINEINPUT H11$: INPUT H22$: LINEINPUT H33$ |
| 25 | PRINT H11$, H22$, H33$ |
| 30 | PRINT "EYES ?" ; LINEINPUT E11$: LINEINPUT E22$: LINEINPUT E33$ |
| 35 | PRINT E11$, E22$, E33$ |
| 40 | PRINT "SKIN ?" ; LINEINPUT S11$: LINEINPUT S22$: LINEINPUT S33$ |
| 45 | PRINT S11$, S22$, S33$ |
| 50 | PRINT "RED ?" ; LINEINPUT R11$: LINEINPUT R22$: LINEINPUT R33$ |
| 55 | PRINT R11$, R22$, R33$ |
| 60 | PRINT "COLOR CODE ?" : LINEINPUT CC$ |
| 65 | PRINT CC$ |
| 70 | PRINT "COLOR DIFF ?" : LINEINPUT CD$ |
| 75 | PRINT CD$ |
| 80 | PRINT "SKIN CARE ?" : LINE INPUT SC$ |
| 85 | PRINT SC$ |
| 90 | PRINT "CLEANSER ?" : LINEINPUT CL$ |
| 95 | PRINT CL$ |
| 100 | PRINT "ASTRINGENT/TONER ?" : LINEINPUT AT$ |
| 105 | PRINT AT$ |
| 110 | PRINT "MOISTURIZER ?" : LINEINPUT MT$ |
| 115 | PRINT MT$ |
| 120 | PRINT "FOUNDATION ?" : LINEINPUT FD$ |
| 125 | PRINT FD$ |
| 130 | PRINT "POWDER ?" : LINEINPUT PD$ |
| 135 | PRINT PD$ |
| 140 | PRINT "BLUSHER ?" : LINEINPUT BL$ |
| 145 | PRINT BL$ |
| 150 | PRINT "LIQUID LINER ?" : LINEINPUT LL$ |
| 155 | PRINT LL$ |
| 160 | PRINT "MASCARA ?" : LINEINPUT MAS$ |
| 165 | PRINT MAS$ |
| 170 | PRINT "LIPSTICK ?" : LINEINPUT LPS$ |
| 175 | PRINT LPS$ |
| 180 | PRINT "LIP GLOSS ?" : LINEINPUT LG$ |

TABLE 10-continued

Listing for Cosmetic Wardrobe Computer Program

| | |
|---|---|
| 185 | PRINT LG$ |
| 190 | PRINT "NAIL GLOSS ?" : LINEINPUT NG$ |
| 195 | PRINT NG$ |
| 200 | PRINT "GLAMOUR ITEMS ?" : LINEINPUT DZ$ : LINEINPUT PP$ |
| 205 | PRINT DZ$, PP$ |
| 207 | PRINT "EYE SHADOW ?" : LINEINPUT SW$ |
| 209 | PRINT SW$ |
| 210 | PRINT "ACCESSORIES ?" : LINEINPUT SA$ : LINEINPUT PFB$ : LINEINPUT LB$ |
| 212 | PRINT "COLOR STICK ?" : LINEINPUT CK$ |
| 214 | PRINT CK$ |
| 215 | PRINT SA$, PFB$, LB$ |
| 216 | PRINT "EYE DISGUISE ?" : LINEINPUT DS$ |
| 400 | REM PRINTING RESULTS OF ANALYSIS |
| 410 | LPRINT TAB(16) "EBBTONE COMPOSITE PERSONAL COLOR HARMONY" |
| 420 | LPRINT " " |
| 430 | LPRINT TAB(35) "FOR" : LPRINT " " |
| 440 | LPRINT TAB (30) NM$ : LPRINT " " |
| 450 | LPRINT "YOU ARE BORN WITH A COLOR COMBINATION THAT HAS COMPLETE IND |
| 460 | LPRINT "AND BEAUTY IN ITS HARMONY. THE COLORS OF YOUR SKIN, HAIR, EYES |
| 470 | LPRINT "RELATED RED FORM WHAT WE CALL YOUR COMPOSITE PERSONAL COLOR |
| 480 | LPRINT "BASED ON THE RESULTS FROM THE EBBTONE PROCESS, YOUR COMPOSI |
| 490 | LPRINT "COLOR HARMONY IS GIVEN BELOW IN THE THREE DIMENSIONS OF COLOR |
| 500 | LPRINT " " : LPRINT " " |
| 510 | LPRINT " ", "HUE", "VALUE", "CHROMA" |
| 520 | LPRINT "COLOR OF HAIR", H11$, H22$, H33$ |
| 530 | LPRINT "COLOR OF EYES", E11$, E22$, E33$ |
| 540 | LPRINT "COLOR OF SKIN", S11$, S22$, S33$ |
| 550 | LPRINT "RELATED RED", R11$, R22$, R33$ |
| 560 | LPRINT"--------------------------------------------------------------------- |
| 620 | LPRINT " " |
| 640 | LPRINT TAB(17) "YOUR EBBTONE PERSONALIZED COSMETIC WARDROBE" |
| 650 | LPRINT " " |
| 660 | LPRINT "THE THEME FOR YOUR EBBTONE PERSONALIZED COSMETIC WARDROBE COL |
| 670 | LPRINT "DETERMINED USING YOUR COMPOSITE PERSONAL COLOR HARMONY. YOUR |
| 680 | LPRINT "COSMETIC WARDROBE COLORS WILL EXPRESS, INTERPRET, AND EXTEND |
| 690 | LPRINT "PERSONAL COLOR THEME." |
| 700 | LPRINT " " |
| 720 | LPRINT "YOUR COLOR CODE IS" ; " " ; CC$ |
| 730 | LPRINT " " |
| 740 | LPRINT "YOUR COLOR DIFFERENCE IS" ; " " ; CD$ |
| 760 | LPRINT " " |
| 780 | LPRINT "SKIN CARE" ; " " ; SC$, "CLEANSER" ; " " ; CL$ |
| 785 | LPRINT " " |
| 790 | LPRINT "MOISTURIZER" ; " " ; MT$, "FOUNDATION" ; " " ; FD$ |
| 795 | LPRINT " " |
| 800 | LPRINT "POWDER" ; " " ; PD$, "BLUSHER" ; " " ; BL$ |
| 805 | LPRINT " " |
| 810 | LPRINT "LIQUID LINER" ; " " ; LL$, "MASCARA" ; " " MAS$ |
| 815 | LPRINT " " |
| 820 | LPRINT "LIPSTICK ?" ; " " ; LPS$, "LIPGLOSS" ; " " ; LG$ |
| 825 | LPRINT " " |
| 830 | LPRINT "NAIL GLOSS" ; " " ; NG$, "ASTRINGENT/TONER" ; " " AT$ |
| 835 | LPRINT " " |
| 840 | LPRINT "DAZZLE DUST" ; " " DZ$, "PUCKER PAINT" ; " " ; PP$ |
| 845 | LPRINT " " |
| 847 | LPRINT "EYE SHADOW" ; " " SW$, "COLOR STICK" ; " " ; CK$ |
| 848 | LPRINT " " |
| 850 | LPRINT SA$, PFB$, LB$, DS$ |

TABLE 11

Color Harmony Data for Color No. 35

| COLOR | HUE | VALUE | CHROMA |
|---|---|---|---|
| HAIR | 4.5 R | 2.3 | 4.5 |
| EYES | 6.7 B | 3.4 | 1.2 |
| SKIN | 3.5 yr | 4.4 | 3.3 |
| RELATED RED | 4.4r | 2.3 | 1.4 |

TABLE 12

Color Harmony Data for Color No. 45

| COLOR | HUE | VALUE | CHROMA |
|---|---|---|---|
| HAIR | 4.5 | 4.5 | 4.5 |
| EYES | 6.7 | 6.7 | 6.7 |
| SKIN | 8.9 | 8.9 | 8.9 |
| RELATED RED | 6.7 | 6.7 | 6.7 |

TABLE 13

Cosmetic Wardrobe Listing for Color No. 35

| COSMETIC | CODE |
|---|---|
| COLOR DIFFERENCE | 1.98 |
| FOUNDATION | DEEP COCOA #11 |
| BLUSHER | TITIAN |
| LIPSTICK | #11 |
| DAZZLE DUST | VIOLET |
| PUCKER PAINT | CURRANT |

TABLE 14

Cosmetic Wardrobe for Color No. 45

| COSMETIC | CODE |
|---|---|
| COLOR DIFFERENCE | 0.456 |
| FOUNDATION | DEEP COCOA #11 |
| BLUSHER | BURGUNDY |
| LIQUID LINER | BROWN |
| MASCARA | BLACK |
| LIPSTICK | 4 |
| LIPGLOSS | 4 |
| DAZZLE DUST | BRONZE FROST |
| PUCKER PAIN | AMETHYST |

Heat-set web offset ink was introduced in the 1950's as a printing process and is used for the production of magazines, catalogues and brochures. All heat-set inks are expected to fulfill exacting criteria, in addition to properties of cold-set ink, such as high gloss and dry quickly in an oven. Heat-set ink are dried by passing the printed web of paper through an oven using high velocity hot air; sufficient to raise the temperature of the to 100–140° C. TAGOS ink has been formulated which meet the criteria of heat-set web offset ink and does not need to be passed through an oven for drying (Tables 15–24). This is accomplished by formulating printing ink using TAGOS of viscosity above 300 poises to obtain high gloss and rub-off resistance. Quick drying is accomplished by using a drying agent.

TABLE 15

Soybean Oligomer Printing Ink - Formula I

| SUBSTANCE | PERCENT |
| --- | --- |
| CARBON BLACK | 20 |
| SOYBEAN OLIGOMER Z - 6 | 71 |
| CLAYTONE HY | 9 |

TABLE 16

Soybean Oligomer Printing Ink - Formula II

| SUBSTANCE | PERCENT |
| --- | --- |
| CARBON BLACK | 20 |
| SOYBEAN OLIGOMER Z - 6 | 70 |
| CLAYTONE HY | 9 |
| COBALT ACETATE | 1 |

TABLE 17

Soybean Oligomer Printing Ink - Formula III

| SUBSTANCE | PERCENT |
| --- | --- |
| CARBON BLACK | 15 |
| SOYBEAN OLIGOMER Z - 10 | 30 |
| SOYBEAN OLIGOMER Z - 3 | 40 |
| CLAYTONE HY | 9 |
| COBALT ACETATE | 1 |

TABLE 18

Soybean Oligomer Printing Ink - Formula IV

| SUBSTANCE | PERCENT |
| --- | --- |
| CARBON BLACK | 20 |
| SOYBEAN OLIGOMER Z - 6 | 61 |
| CLAYTONE HY | 9 |
| POLYOL | 10 |

TABLE 19

Cottonseed Oligomer Printing Ink - Formula V

| SUBSTANCE | PERCENT |
| --- | --- |
| CARBON BLACK | 20 |
| COTTONSEED OLIGOMER | 71 |
| CLAYTONE HY | 9 |
| COBALT ACETATE | 1 |

TABLE 20

Sunflower Seed Oligomer Printing Ink - VI

| SUBSTANCE | PERCENT |
| --- | --- |
| CARBON BLACK | 20 |
| SUNFLOWERSEED OLIGOMER | 71 |
| CLAYTONE HY | 9 |
| COBALT ACETATE | 1 |

TABLE 21

Corn Oligomer Printing Ink - VII

| SUBSTANCE | PERCENT |
| --- | --- |
| CARBON BLACK | 20 |
| CORN OLIGOMER | 71 |
| CLAYTONE HY | 9 |
| COBALT ACETATE | 1 |

TABLE 22

N,N'-di-n-butyl-$N_a$-lauroyl Glutamide(BLG)
Soybean Oligomer Printing Ink - VIII

| SUBSTANCE | PERCENT |
| --- | --- |
| CARBON BLACK | 20 |
| BLG-SOYBEAN OLIGOMER* | 71 |
| CLAYTONE - HY | 9 |

*Preparation given in Section VI

TABLE 23

Thermosetting Epoxy Printing Ink

| SUBSTANCE | PERCENT |
| --- | --- |
| EPOXY(I) SOYBEAN* | 70 |
| PHTHALO BLUE PIGMENT | 15 |
| SOLVENT | 5 |
| HyTONE | 5 |

*See Section IX

TABLE 24

Fountain Solution

| SUBSTANCE | PERCENT |
| --- | --- |
| A B DICK UNIVERSAL | 95 |
| T-BUTYL HYDROPEROXIDE | 5 |

In screen printing the ink is forced through the open areas of a stencil supported on a mesh of synthetic fabric stretched across a frame. The ink is mechanically forced through the mesh onto the substrate underneath by drawing a squeegee across the stencil. These inks are high viscosity, low tack, short cure times, and good color retention after several wash cycles. TAGOS were formulated to meet these criteria (Tables 25–31).

TABLE 25

Screen Printing Ink - Formula I

| SUBSTANCE | PERCENTAGE |
| --- | --- |
| CI PIGMENT RED 49 | 20 |
| SUNFLOWERSEED OLIGOMER | 30 |
| SOYBEAN OLIGOMER Z - 6 | 50 |

TABLE 26

Screen Printing Ink - Formula II

| SUBSTANCE | PERCENTAGE |
| --- | --- |
| CI PIGMENT RED 49 | 20 |
| SUNFLOWERSEED OLIGOMER | 30 |
| SOYBEAN OLIGOMER X - Y | 50 |

TABLE 27

Screen Printing Ink - Formula III

| SUBSTANCE | PERCENT |
| --- | --- |
| CI PIGMENT RED 49 | 20 |
| SUNFLOWERSEED OLIGOMER Z-6 | 30 |
| SOYBEAN OLIGOMER Z-6 | 25 |
| SOYBEAN OLIGOMER X - Y | 25 |

TABLE 28

Screen Printing Ink - Formula IV

| SUBSTANCE | PERCENT |
| --- | --- |
| BLUE DYE | 10 |
| SOYBEAN OLIGOMER Z - 6 | 25 |
| WATER | 74.98 |
| THICKNER | 0.1 |
| COBALT ACETATE | 0.1 |

TABLE 29

Screen Printing Ink - Formula V

| SUBSTANCE | PERCENT |
| --- | --- |
| BLUE DYE | 10 |
| COTTONSEED OLIGOMER | 25 |
| WATER | 74.98 |
| THICKNER | 0.1 |
| COBALT ACETATE | 0.1 |

TABLE 30

Screen Printing Ink - Formula VI

| SUBSTANCE | PERCENT |
| --- | --- |
| BLUE DYE | 10 |
| SUNFLOWERSEED OLIGOMER | 25 |
| WATER | 74.98 |
| THICKNER | 0.1 |
| COBALT ACETATE | 0.1 |

TABLE 31

Screen Printing Ink - Formula VII

| SUBSTANCE | PERCENT |
| --- | --- |
| BLUE DYE | 10 |
| CORN OLIGOMER | 25 |
| WATER | 74.98 |
| THICKNER | 0.1 |
| CORN | 0.1 |

The inks were printed on cotton and coated cotton fabrics and allowed to dry. The printed fabrics were then washed and dried. The color was measured before and after each wash cycle to determine color fastness (Tables 32–33).

TABLE 32

Color Fastness of Screen Printed Uncoated Cotton Fabrics

| INK FORMULA | L* | a* | b* | L* | a* | b* | Gray Change- | Difference |
| --- | --- | --- | --- | --- | --- | --- | --- | --- |
| I | 36.31 | 43.35 | 12.60 | 37.59 | 38.00 | 9.97 | 3.00 | 6.10 |
| II | | | | | | | | |
| III | | | | | | | | |
| IV | 38.99 | −14.21 | −39.57 | 40.96 | −12.85 | −35.00 | 3.00 | 5.16 |
| V | | | | | | | | |
| VI | | | | | | | | |
| VII | | | | | | | | |

TABLE 33

Color Fastness of Screen Printed Coated Cotton Fabrics

| INK FOR- | COLOR BEFORE | | | COLOR AFTER | | | Gray Change- | |
| --- | --- | --- | --- | --- | --- | --- | --- | --- |
| MULA | L* | a* | b* | L* | a* | b* | Difference | |
| I | 37.63 | 47.09 | 12.42 | 39.55 | 44.52 | 9.44 | 3.00 | 4.37 |
| II | | | | | | | | |
| III | | | | | | | | |
| IV | 38.99 | −14.21 | −39.57 | 40.96 | −12.85 | 35.00 | −3.00 | 5.16 |
| I | | | | | | | | |

Although many valuable products are fabricated each day from fibers, these items could never exist unless a finish had been applied to the fibers during the extrusion or spinning process. Fabric finishing is intended to provide a special performance characteristics or properties to a textile fabric. This can be the development of dimensional control or resistance to wrinkling during use. The characteristics may be the provision of permanent crease and smooth drying performance or the requirement for the fabric to withstand subsequent processing steps. There may be the need for a finish to impart resistance to end use exposure, i.e., water or oil repellency or resistance to crocking or bleeding. Of equal importance is the need to provide the finished fabric with improved or changed aesthetic properties. TAGOS were developed for applications in sizing and finishing.

Solutions to size fabrics were made according to the formula given in Table 34. TAGOS were soybean, cottonseed, sunflower seed, and corn. Strips of gauzy cotton fabric (5×30 cm were padded twice at 25 C to ca. 110% wet pick-up, followed by drying at 120 C for 3 minutes and conditioning for 48 hours at 65% relative humidity and at room temperature.

Textile finishers were made using soybean, cottonseed, sunflower seed, and corn oligomers according to the formula given in Table 35. Poplin cotton fabric pieces (30×45 cm) were padded twice at room temperature in the finish solution to ca. 80% wet pick-up, followed by drying (100 C/3 min.) and curing (160 C/3 min.). The cured samples were then given an after wash in a bath containing 1 g/l sodium carbonate along with 1 g/l on triton X-100 at 55 C for 15 minutes./rinsed, and air dried, and conditioned.

TABLE 34

Formula for Textile Sizers

| SUBSTANCE | PERCENTAGE |
|---|---|
| TAGO | 12 |
| TRITON X - 100 | 5 |
| WATER | 83 |

TABLE 35

Formula for Textile Finishers

| SUBSTANCE | PERCENTAGE |
|---|---|
| TAGO | 25 |
| WATER | 65 |
| MAGNESIUM CHLORIDE HEXAHYDRATE | 5 |
| TRITON X-100 | 5 |

Historically, reactions on polymers have been of major importance, as they have made possible the applications of cellulose as textile fibers, plastics, coatings, and even explosives. Reactions of polymers can occur with oxygen, irradiation, heat, moisture, and bacterial attack which induces the problem of "aging" of polymeric materials. The most important of them are atmospheric oxygen and irradiation, since they are most likely to induce chain scission. Polymers can undergo chemical reactions by chemical modification of the functional groups of the polymers. As discussed earlier, a Diels-Alder diene synthesis was used as a basis for explaining the polymerization of TAGOS which is most often referred to in the literature. Most investigators agree with the formation and presence of hydroxyl groups, carboxylic acid groups, cyclic compounds, and double bonds during thermal polymerization. These functional groups, along with the ester group, provide the basis for producing polymers from TAGOS.

An equivalency based on hydroxyl number of the glycol and assumed hydroxyl number of TAGOS per molecule was calculated. The hydroxyl number for glycol was two and the hydroxyl number for TAGO varied for each experiment. The equivalency mass for glycol was the molecular weight divided by two. The equivalency mass for TAGOS was obtained by dividing the apparent molecular weight by the hydroxyl number for each experiment. Apparent molecular weights were determined by gel permeation chromatography. An illustrative example was the formation of complexes between soybean oligomer (SBO) and ethylene and propylene glycol (Table 36). The apparent molecular weight of SBO was 10,000.

A series of experiments were conducted using N,N'-di n-butyl-$N_a$-lauroyl glutamide (BLG) to crosslink TAGOS. One gram of BLG was dissolved in 99 grams of TAGOS and heated to 150° C. The solution viscosity increased depending on the amount of BLG added.

TABLE 36

Triacylglycerol Oligomer Complexes with Ethylene and Propylene Glycol

| TAGOS | VISCOSITY | HYDROXYL* | MOL. WT. | GLYCOL | RATIO | VISCOSITY |
|---|---|---|---|---|---|---|
| SOYBEAN | 22683 cp | 10 | 10000 | ETHYLENE | 1::1 | 17733 cp |
| SOYBEAN | 22683 cp | 10 | 140000 | PROPYLENE | 1:01 | 17983 cp |

When ethylene glycol, 10 grams, was mixed with SBO, 300 grams, the solution thickened and became very turbid. The mixture was heated up to a temperature of 120° C. and a white vapor was given off. The mixture was removed from the hot plate for thirty minutes after which time the mixture was replaced on the hot plate and heating continued. No vapors were given off after heating for 3.75 hours. After heating for more than six hours the mixture became completely clear with the appearance of small crystal like substances at the bottom of the flask. After more than nine hours of heating, the mixture was removed from the heat and allowed to cool. As it cooled down to room temperature it became a turbid viscous mixture.

SBO, 306 grams, was mixed with propylene glycol, 10 grams, in an Erlenmeyer flask. The mixture remained clear after mixing. The mixture was heated to a temperature of 120° C. The mixture was heated to a temperature of 115° at which time white vapors were given off. However, the mixture remained clear. After more than eight hours of heating, the mixture was removed from the hot plate and cooled to room temperature. At room temperature, the mixture became very turbid and viscous.

Emulsion polymerization of linseed and safflower acrylates and methacrylactes were prepared by Joshi (1978). The alcohol were first prepared by Rheberg's (1946) procedure involving the alcoholysis of methyl acrylate or methyl methacrylate in the presence of an acid catalyst and a polymerization inhibitor. In a one liter, two-necked round-bottomed flask are placed 200 grams of soybean resin and 50 grams of methyl acrylate, 2 grams of hydroquinone, and 500 milligrams of p-toluene sulfonic acid. The flask is attached to an all-glass fractionating column without packing and the solution is heated to a temperature of 100° C. using a heating mantle and stirred with a magnetic stirrer. The column is operated under total reflux until the temperature of the vapors at the still head falls to 62–63° C. which is the boiling point of the methanol-methyl acrylate azeotrope. This azeotrope then distilled as rapidly as it is formed, the temperature at the still head not being allowed to exceed 65° C. When the production of methanol has become very low (6–10 hours), the excess methyl acrylate is distilled. The soybean resin methacrylate mixture is extracted with suitable solvent(s) to remove the hydroquinone and p-toluene sulfonic acid. The soybean resin methacrylate is characterized by IR spectroscopy. All polymerization reactions were carried out in emulsion using the standard procedure of Fisher and Mast (1940) suitably modified to meet our requirements. The exact procedure followed is described below. A 250 ml capacity ground-glass joint Erlenmeyer flask, carrying a Teflon-enclosed magnetized stirring bar and fitted with a reflux condenser, is charged with 40 ml of deionized water, 200 mg of Triton X-100, 200 mg of SLS-Liquid, and 1–2 mg of ammonium persulfate. The solution is stirred slowly on a hot plate with magnetic stirring, and 50 grams of soybean resin methyacrylate is added into it. Heat is initially applied to induce polymerization and thereafter continued at a rate just sufficient to cause gentle refluxing. The polymerization is considered to be completed when the emulsion becomes very viscous. The viscous material is then shaken with warm water and the suspension centrifuged. The process is repeated two or three times to remove the surfactant completely. The mass is then dried in a vacuum and films cast on tin plates (1 mil, dry).

Vinyl and allyl ester of soybean resin were prepared using the method of Swern and Jordan (1948). In a 500-ml round bottom three-necked flask provided with a thermometer, a reflux condenser, and a gas inlet tube through which steam or nitrogen is passed are placed 100 grams of freshly of freshly distilled vinyl acetate and grams of 200 grams of soybean resin viscosity Z-6. and 1.6 grams of mercuric acetate is added. The mixture is shaken by hand for about 30 minutes, and 0.15 ml of 100% sulfuric acid is added dropwise. The solution is heated under reflux for 3 hours, then 0.83 grams of sodium acetate trihydrate is added to neutralize the acid. The excess vinyl acetate is recovered by distillation at atmospheric pressure (vapor temperature about 70–80° C.) until the solution temperature reaches 125° C. The distillation is completed at 10 mm of Hg or lower.

Polymerization is carried out in one ounce screw cap bottles equipped with oil resistant gaskets and perforated caps so that small samples could be removed with a hypodermic syringe without opening the bottles. The bottles were charged with soybean resin vinyl ester and 3% d-t-butyl peroxide. The bottles were heated by suspending them in an oil-bath maintained at the desired temperature. The polymers are isolated by stripping the monomers in vacuo (0.1 mm) at a maximum temperature of 200° C., and extracting the residue repeatedly with methanol.

Soybean X—Y, TAGO 310 grams, is added into a closed reactor and purged with nitrogen for a few minutes. The oligomer is heated to about 260° C. with constant stirring. The stirring is continued throughout the reaction. Dicyclopentadiene, 104 ml, is added at a slow addition rate of 0.4 to 0.6 ml/min at the bottom of the vessel under the hot TAGO. After the addition of dicyclopentadiene is complete, the reaction mixture is kept at 260° C. for 3.5 hours with stirring. Then the mixture is stripped at 1 mm Hg for 30 minutes and removed from the reaction vessel. The product is cooled to room temperature.

Soybean oligomer Z-6(TAGO), 500 grams, is heated to 145° C. and 1000 g of myrcene and 10 grams of di-tert-bu peroxide is added. The reaction is continued for 6 hours at 140–150° C. The modified TAGO is treated with 0.05% Co and heated in a dryer.

Vegetables oils as an alternative diesel and fossil fuel is limited by their high viscosity. Several routes have been tried for reducing this viscosity and most recently has been the direct catalytic upgrading of the vegetable oils to produce liquid fuels. The catalytic cracking of vegetable oils, which is nothing more than reduction of the molecular weight and viscosity, gives several types of products, either gaseous, solid, or liquid. Numerous reports are given in the literature for the catalytic cracking of soybean oil and other vegetable oils. Most investigations have shown that the products obtained from the cracking process are comparable to diesel fuel but not to fossil fuel. The physical properties and chemical compositions of bio and fossil fuels were determined by Pioch (1993). The results showed that the aromatic content of fossil fuel is higher than the aromatic content of biofuels. The olefin content is in the same range as well as the saturated branched chain hydrocarbons. The octane number for fossil fuel was reported as 90 and that of catalytically cracked copra and palm stearine were 91 and 86, respectively. Concerning the diesel fractions, the chemical compositions are close to the fossil fuels. The biodiesel fuel had a high content of normal paraffin, no olefins and no heavy hydrocarbons and similar aromatic content as the fossil diesel fuel. Kobayashi (1921) distilled soybean and coconut oil mixed with kaolin at approximately 700° C. decomposed to give "vegetable petroleum" or biofuel. During world war II, Chang (1947) reported that large scale decomposition of tung oil and soybean oil was carried out in large scale batch reactors in China, with the use of acid ($AlCl_3$) or basic (MgO, CaO, NaOH) catalysts.

Attempts to produce fuel that could be gasoline substitute, i.e., contain a significant fraction of aromatics are reported in the literature. Novella (1984) applying ZSM-5 type zeolites in acid form transformed various kinds of vegetable oils to hydrocarbon fuel. The use of soybean oligomer as a feed stock for catalytic cracking to increase the aromatic content of biofuels is evident from the proposed chemical structure of the repeating unit. As described in the introduction, the Diels-Alder diene synthesis has received the most support from data collected for the polymerization mechanism of TAGS. This mechanism, wherein a diene and a dienophile combine to form a cyclohexene structure, is supported by data showing the presence of cyclic structures in polymerized oils. It is therefore proposed to investigate the formation of biofuels with high aromatic content by reductive catalytic hydrocracking of TAGOS of differing viscosity. Filho (1993) reported a production yield (weight % of feed) using soybean oil of 66.6% alkanes, 11.9% cycloalkanes, 4.3% alkylbenzenes. The authors concluded that depending upon the multifunctionality of the catalyst, isomerization, cyclization, and aromatization processes can occur during hydrocarbon fuel production from vegetable oils. Using a similar approach with the resin, it is the expectation to obtain a biofuel that is high in aromatic content comparable to fossil fuel due to existence gcyclic structures in TAGOS.

Reductive catalytic hydrocracking will be with either a two gallon or a 50 cm$^3$ (Autoclave Engineering) stainless steel batch reactor equipped with a stirrer, and the temperature and pressure limits being 450° C. and 25 MPa, respectively. The feedstock consists of soybean resin with viscosity of 500 poises and 1000 poises using catalysts precursors of NiMo/—Al$_2$O$_3$ and Ni/SiO$_2$ (2 wt % based on resin) and elemental sulfur (1.7 5 wt % based on resin). The procedure of Filho (1993) was followed.

Maplewood shavings, 16.1 grams, and soybean oligomer Z-6, 53.5 grams, were mixed together until all shavings of maplewood were covered with the oligomer. The mixture was placed in a 8½ cm diameter ×7 mm thick brass dish. Hot air was blown over the mixture for one hour. The mixture was placed in a convection oven at 75° C. for 26 hours. The board was removed and allowed to cool to room temperature and examined. The board was spongy.

Addition of sodium hydroxide to soybean Z-6 on standing formed a solid polymer film.

Addition of sodium hydroxide to soybean X—Y on standing formed a turbid solution and a lot of foam when shaken.

Lawn grass with long stems and long blade-like leaves was cut into small pieces and dried. The grass sample was then placed into a mill and reduced to small fragments. A small mesh screen was used to separate the smallest pieces from the larger pieces. The smaller pieces were used for the preparation. Grass, 2.0 grams, was mixed with SBO, 200 grams, in an Erlenmeyer flask. The mixture was stirred and placed on a hot plate. After approximately one hour of heating, the mixture turned a very dark green. The mixture was heated for a total of twenty one hours, removed from the hot plate and allowed to cool to room temperature. The viscosity of the mixture was determined (Table 37).

TABLE 37

Viscosity Data for Complex Between Triacylglycerol Oligomers and Gramineae (Grass)

| TAGOS | TAGO VISCOSITY | COMPLEX VISCOSITY |
|---|---|---|
| SOYBEAN | 22,683 cp | 33,367 cp |
| COTTONSEED | | |
| SUNFLOWERSEED | | |
| CORN | | |

Johnson's pure cotton balls, made from 100% pure, non-chlorine bleached cotton, was purchased from a local drug store. One cotton, which weighed 0.3 grams, was pulled into small pieces and added one at a time to an Erlenmeyer flask containing 203 grams of SB(Z-6) which had been heated to 100° C. The mixture was stirred and placed on a hot plate. After heating for approximately seven hours at 110° C., the cotton started to form gelatinous mass. It was not observable whether the liquid portion of the mixture was also becoming more gelatinous. Continued heating of the mixture resulted in the cotton becoming almost completely gelatinous. The mixture was removed from the hot plate after 40 hours of heating. The viscosity of the liquid portion was measured (Table 38).

TABLE 38

Data for Complex Between Triacylglycerol Oligomers and Cotton

| TRIACYLGLYCEROL OLIGOMER | COMPLEX VISCOSITY, P |
|---|---|
| SOYBEAN (Z-6) | >8,000,000 cp |
| COTTONSEED | |
| SUNFLOWERSEED | |
| CORN | |

Removal of ink from paper substrate is done commercially using ink removal solutions containing hazardous materials. It has been previously shown that TAGOS can be emulsified using water and a surfactant. Paper printed with TAGOS inks are easily dissolved in a solvent system using non-hazardous, water-based, cleaning solutions which emulsifies the ink and can be reused several times before it has to be replaced. The ink solution is filtered to remove the deinked paper slurry which can then be further processed to produce recycled paper.

TABLE 39

Formulation of Ink Removal Solution #1

| CONSTITUENT | PERCENT |
|---|---|
| PART A* | 89.07 |
| WATER | 85.07 |
| SWS | 0.1122 |
| DYE | 1.68 |
| MONOETHA NOLAMINE | 2.25 |
| NA4EDTA | 2.81 |
| DIPROPYLENEGL; YCOLMETHYLETHER | 3.37 |
| WITCONATE 90 K | 4.27 |
| PART B* | 10.93 |
| TRITON X-100 | 64.04 |
| HYAMINE | 8.51 |
| SCENT | 27.45 |

TABLE 40

Formulation of Ink Removal Solution #2

| CONSTIUENT | PERCENT |
|---|---|
| TRITON X-100 | 1 |
| POTASSIUM HYDROXIDE (37.4%) | 13.37 |
| WATER | 85.63 |

Approximately three drops of red ink was placed on a 5"×8" piece of white paper and drawn down with a putty knife making an ink strip approximately 3" in width. A length of approximately 2" was cut and used for the test.

In one Erlenmeyer flask was placed 100 ml of formula #1 (Table 39) cleaning solution along with the test specimen. In another Erlenmeyer flask was placed 100 ml of formula #2 (Table 40) cleaning solution along with the test specimen. Both solutions were shaken and allowed to stand. Periodically on several occasions they were shaken again. Ink began to be removed immediately with formulation #1 as evidence by the solution forming a reddish color. With formulation #2 color was being removed as evidence by the fading of the test specimen.

The mixture obtained from printed paper is filtered and the solution decanted. The paper slurry remaining is mixed with and emulsion prepared using soybean oligomer Z-6 (25%), triton X-100(5%), and water (70%). The mixture is filtered and then dried by passing through pads heated to 75° C. A sheet of recycled paper is formed.

TAGOS interaction with metals and water were examined. The examination was to determine differences in the interaction between metal-TAGO complex and water-TAGO complex. Soybean oligomer Z-6 and X—Y, 5 grams each, were placed in separate containers of 95 grams of distilled water. The mixtures were stirred and allowed to stand at room temperature. The same procedure was repeated with 0.2 m potassium hydroxide solution.

Both soybean oligomers X—Y and Z-6 had formed two layers. The aqueous layer was slightly turbid and a white oily layer. Upon standing at room temperature for a long period of time, soybean oligomer Z-6 formed a rubbery, spongy mass. This mass is probably due to the interaction of air, water and the oligomer.

Water was added to a beaker which contained soybean oligomer crosslinked with BLG. The mixture was heated to boiling. The sides of the beaker were scraped with a spatula. Upon cooling, polymer particles were floating in the water. The particles were removed from the water and allowed to dry. Upon drying, the small particles formed clear plastic pieces. The plastic pieces were very elastic and stretched when pulled. The plastic pieces were soft and spongy.

Upon addition of 0.2 m KOH to soybean oligmer X—Y, the solution turned milky white with no formation of oil droplets. A foamy layer was on top. Upon addition of 0.2 m KOH to soybean oligmer X-6, it also formed a milky/cloudy solution with a foamy layer on top. However, upon standing for a long period of time, soybean oligomer X—Y produces large amount of foam when shaken with no visible large particles present. The solution, however, is still turbid. In the case of soybean oligomer Z-6, the mixture does not produce a lot of foam when shaken, and it contained solid particles.

Thus, in accordance with the present invention, there has been provided triacylglycerol oligomers and methods for making and using same that fully satisfies the objectives and advantages set forth above. Although the invention has been described in conjunction with the specific drawings and language set forth above, it is evident that many alternatives, modifications, and variations will be apparent to those skilled in the art. Accordingly, it is intended to embrace all such alternatives, modifications and variations that fall within the spirit and broad scope of the invention.

What is claimed is:

1. A method for separating lecithin from a lecithin-bulk mixture, comprising the steps of:
    introducing a lecithin-bulk mixture into a separator to obtain a concentrated lecithin mixture, the lecithin-bulk mixture being a product resulting from a reaction of a triacylglycerol mixture and a liquid medium;
    introducing the concentrated lecithin mixture onto a porous material, the porous material allowing the liquid medium to pass through while retaining a wet lecithin;
    introducing the wet lecithin into a series of pressurized and heated rollers to remove moisture to produce a sheet of lecithin; and
    introducing the sheet of lecithin into an oven wherein the sheet of lecithin is reduced to having a moisture content of less than three percent.

2. The method of claim 1 wherein the liquid medium is water.

3. The method of claim 1 wherein at least a pair of the series of rollers is stainless steel.

4. The method of claim 1 wherein at least a pair of the series of rollers is rubber.

5. The method of claim 1 wherein the series of rollers are in contact with one another.

* * * * *